United States Patent
Callahan

(10) Patent No.: US 7,162,039 B1
(45) Date of Patent: *Jan. 9, 2007

(54) NOISE BARRIER APPARATUS HAVING ACOUSTIC WAVE DAMPING CUSHIONS

(75) Inventor: Thomas F. Callahan, Grantham, NH (US)

(73) Assignee: Matthew G. Callahan, Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/522,834

(22) Filed: Mar. 10, 2000

Related U.S. Application Data

(63) Continuation-in-part of application No. 09/340,813, filed on Jun. 28, 1999, now abandoned, which is a continuation of application No. 08/803,674, filed on Feb. 21, 1997, now Pat. No. 5,917,918, application No. 09/522,834, which is a continuation-in-part of application No. 09/129,797, filed on Aug. 6, 1998.

(60) Provisional application No. 60/055,395, filed on Aug. 6, 1997, provisional application No. 60/012,168, filed on Feb. 23, 1996.

(51) Int. Cl.
*A61B 7/04* (2006.01)
(52) U.S. Cl. .......................... 381/67; 381/380; 381/374
(58) Field of Classification Search ................. 381/67, 381/309, 328, 72, 74, 380, 382, 372, 371, 381/376; 181/130–131, 135, 129
See application file for complete search history.

(56) References Cited

U.S. PATENT DOCUMENTS

| | | | |
|---|---|---|---|
| 1,279,396 A | 9/1918 | Michelson et al. | |
| 2,385,211 A | 9/1945 | Konrad | |

(Continued)

FOREIGN PATENT DOCUMENTS

| | | |
|---|---|---|
| WO | 97/30634 | 8/1997 |

OTHER PUBLICATIONS

David Clark Co., Inc., Model H2O-10, Jul. 29, 1997 David Clark Co., Inc. Parts List for the H2O-20 and H2O-16, Jul. 29, 1997.

(Continued)

*Primary Examiner*—Ping Lee
(74) *Attorney, Agent, or Firm*—Michael J. Weins; Jeffrey E. Semprebon

(57) ABSTRACT

The present invention provides a noise barrier apparatus for inhibiting external noise from causing the presence of noise in an audio chamber defined by a noise barrier device and including the user's ear canal. The noise barrier apparatus may be constituted by an in-ear noise barrier device or devices or an over-the-ear device or devices. An in-ear application of the present invention provides an in-ear-canal audio receiver comprising an in-ear-canal adapter body having a tapered ear plug portion that is inserted into the user's ear canal. The adapter body further has an opening in the plug portion, an exterior annular indent, and an inner chamber coupled to the opening of the plug portion. The inner chamber of the in-ear-canal adapter body holds a transducer assembly comprising a transducer housing and a transducer or speaker. The transducer is positioned in a passage extending through the transducer housing. A torus-shaped cushion is positioned in the annular indent of the in-ear-canal adapter body. The cushion provides comfort and establishes a good seal with the user's ear, and also provides mechanical damping to inhibit propagation of external acoustic pressure waves via the noise barrier device to an audio chamber including an interior of the noise barrier device and the user's ear canal. An over-the-ear application of the present invention provides an ear cup and has a torus-shaped cushion at an interface part thereof which bears against the side of the user's head at an area surrounding the user's ear. The cushion again provides comfort, establishes a good seal with the user's head and provides mechanical damping to inhibit propagation of external acoustic pressure waves via the noise barrier device to an audio chamber including an interior of the noise barrier device and the user's ear canal. The cushion is preferably formed of a material which is at least partially plastically deformable and provides a damping ratio greater than 0.75.

14 Claims, 17 Drawing Sheets

U.S. PATENT DOCUMENTS

| | | | |
|---|---|---|---|
| 3,080,011 A | 3/1963 | Henderson | |
| 3,415,246 A | 12/1968 | Hill | |
| 3,448,224 A | 6/1969 | Giller | |
| 3,663,973 A | 5/1972 | Spence | |
| 3,732,382 A | 5/1973 | DeWitt | |
| 3,737,930 A | 6/1973 | Smith, III | |
| 3,783,201 A | 1/1974 | Weiss et al. | |
| 3,852,540 A | 12/1974 | Diethelm | |
| 3,908,200 A | 9/1975 | Lundin | |
| 4,006,796 A | 2/1977 | Goehorst | |
| 4,048,444 A | 9/1977 | Giampapa | |
| 4,055,233 A | 10/1977 | Huntress | |
| 4,170,275 A | 10/1979 | Larsen | |
| 4,261,432 A | 4/1981 | Gunterman | |
| 4,299,303 A * | 11/1981 | Clark | 181/131 |
| 4,456,642 A | 6/1984 | Burgdorfer et al. | |
| 4,471,496 A | 9/1984 | Gardner, Jr. et al. | |
| 4,540,063 A | 9/1985 | Ochi et al. | |
| 4,658,931 A * | 4/1987 | Curry | 381/372 |
| 4,671,265 A | 6/1987 | Andersson | |
| 4,674,134 A | 6/1987 | Lundin | |
| 4,811,402 A | 3/1989 | Ward | |
| 4,856,118 A | 8/1989 | Sapiejewski | |
| 4,878,560 A * | 11/1989 | Scott | 381/380 |
| 4,913,259 A | 4/1990 | Packard | |
| 4,937,876 A | 6/1990 | Biermans | |
| 4,953,215 A | 8/1990 | Weiss et al. | |
| 4,958,697 A | 9/1990 | Moody | |
| 4,972,491 A | 11/1990 | Wilcox, Jr. | |
| 4,985,925 A | 1/1991 | Langberg et al. | |
| 4,989,271 A | 2/1991 | Sapiejewski et al. | |
| 5,020,163 A | 6/1991 | Aileo et al. | |
| 5,048,090 A | 9/1991 | Geers | |
| 5,073,947 A | 12/1991 | Reddemann et al. | |
| 5,113,428 A * | 5/1992 | Fitzgerald | 455/575.2 |
| 5,138,722 A | 8/1992 | Urella et al. | |
| 5,208,867 A | 5/1993 | Stites, III | |
| 5,243,709 A | 9/1993 | Sheehan et al. | |
| 5,276,740 A | 1/1994 | Inanaga et al. | |
| 5,288,953 A | 2/1994 | Peart | |
| 5,298,692 A | 3/1994 | Ikeda et al. | |
| 5,305,387 A | 4/1994 | Sapiejewski | |
| 5,319,163 A | 6/1994 | Scott | |
| 5,327,506 A | 7/1994 | Stites, III | |
| 5,333,206 A | 7/1994 | Koss | |
| 5,345,509 A | 9/1994 | Hofer et al. | |
| 5,396,563 A | 3/1995 | Yoshimi | |
| 5,448,637 A | 9/1995 | Yamaguchi et al. | |
| D391,575 S | 3/1998 | Bergin et al. | |
| 5,917,918 A | 6/1999 | Callahan | |
| 6,187,232 B1 * | 2/2001 | Chaudhary et al. | 264/51 |
| 8,265,475 * | 7/2001 | Chifei et al. | 524/127 |

OTHER PUBLICATIONS

David Clark Co., Inc., Aviation Accessories, Jul. 29, 1997 David Clark Co., Inc., Aviation Headsets, 1994.

David Clark Co., Inc., Headset Accessories, 1993 David Clark Co., Inc., Hearing Protectors, Jul. 1993.

Etymotic Research ER-48/ER-4S Canal Phone™ Earphones User's Manual.

* cited by examiner

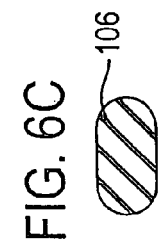
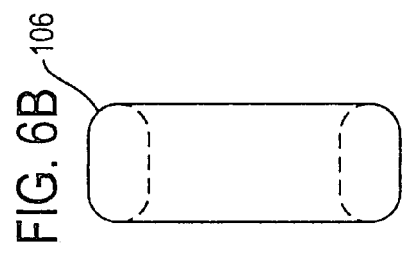
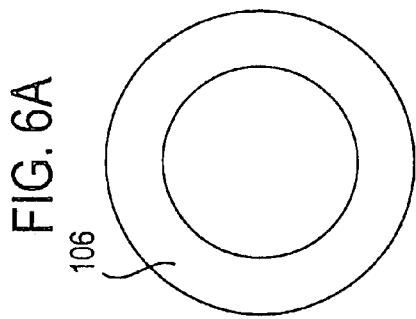
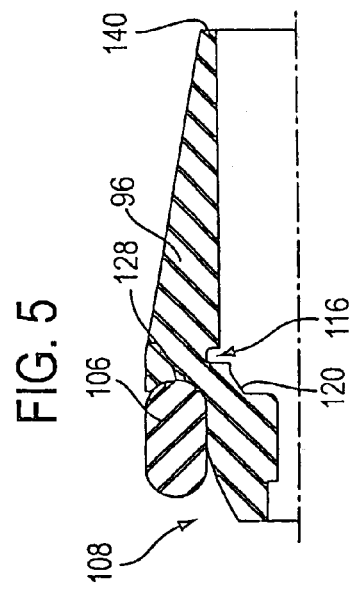
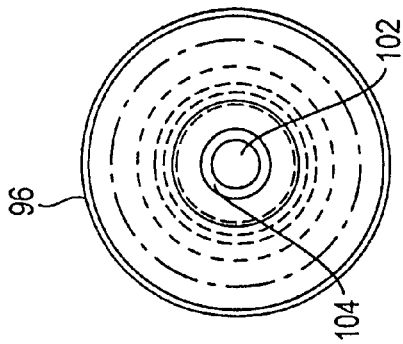
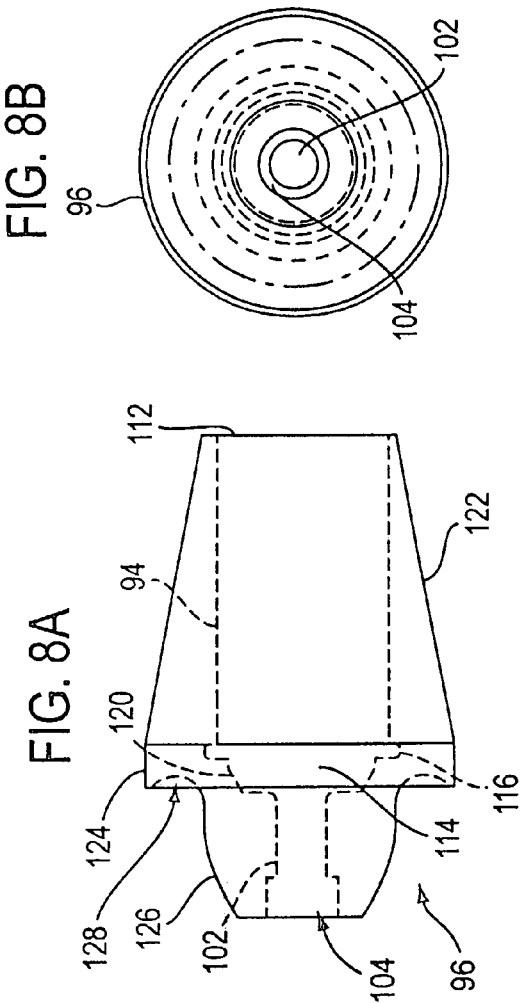
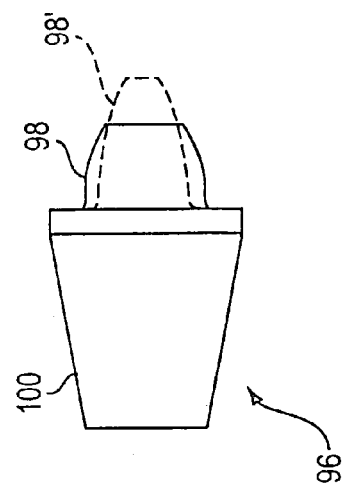

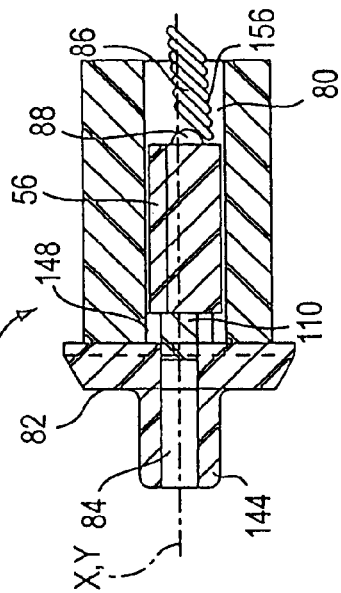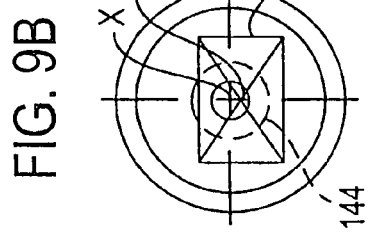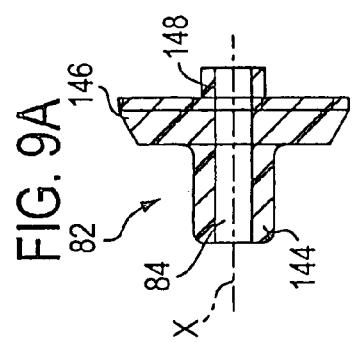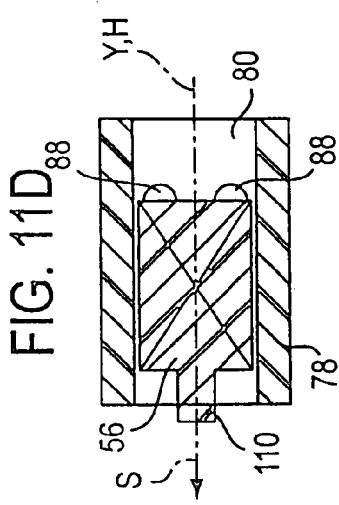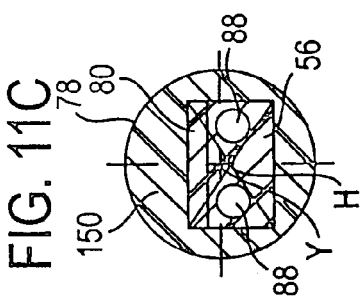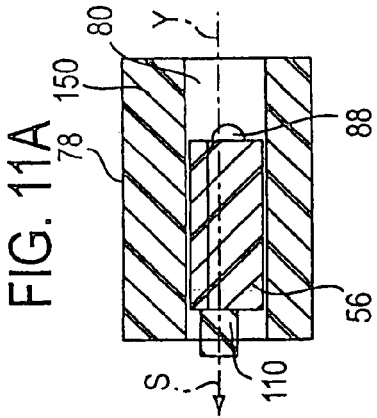

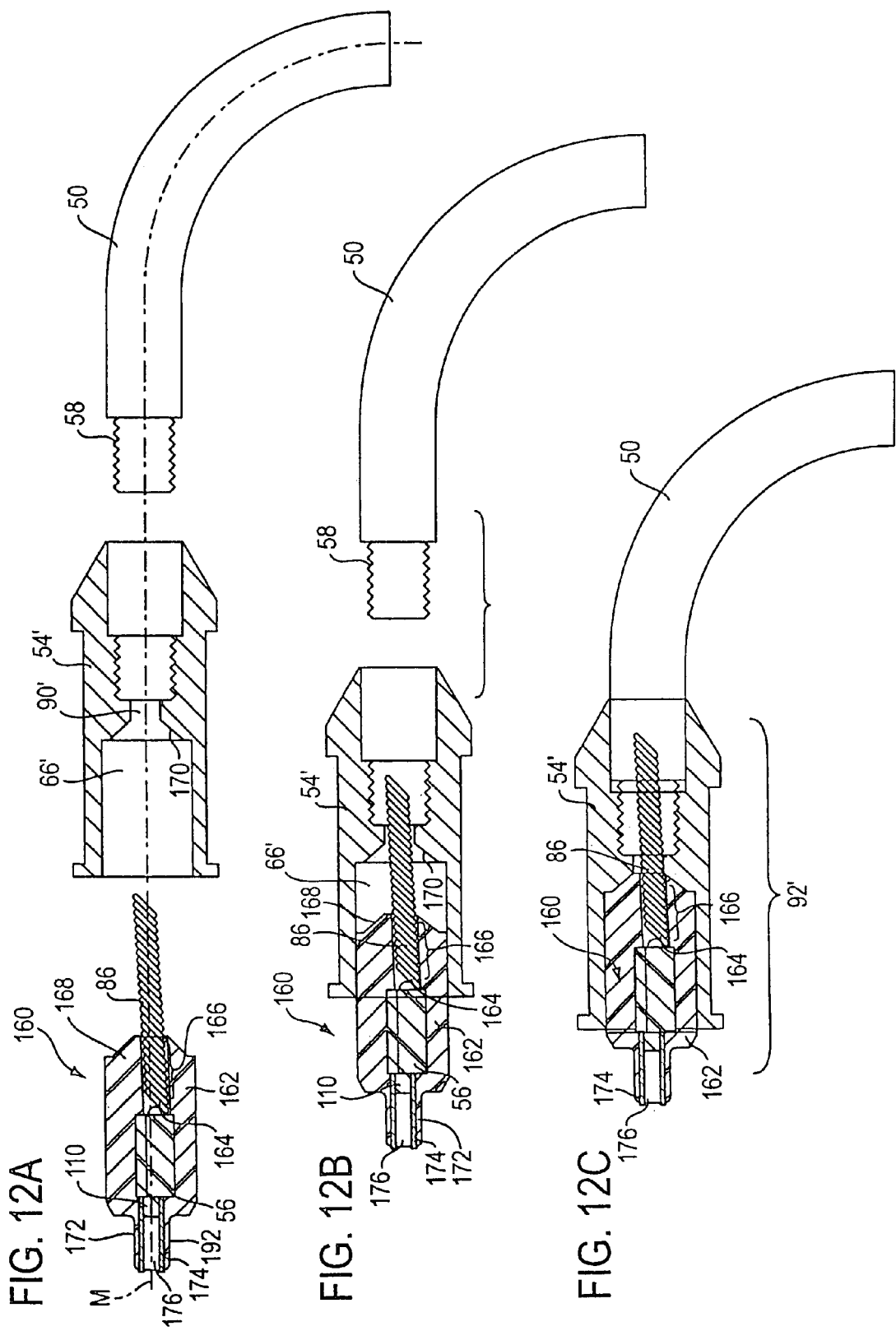

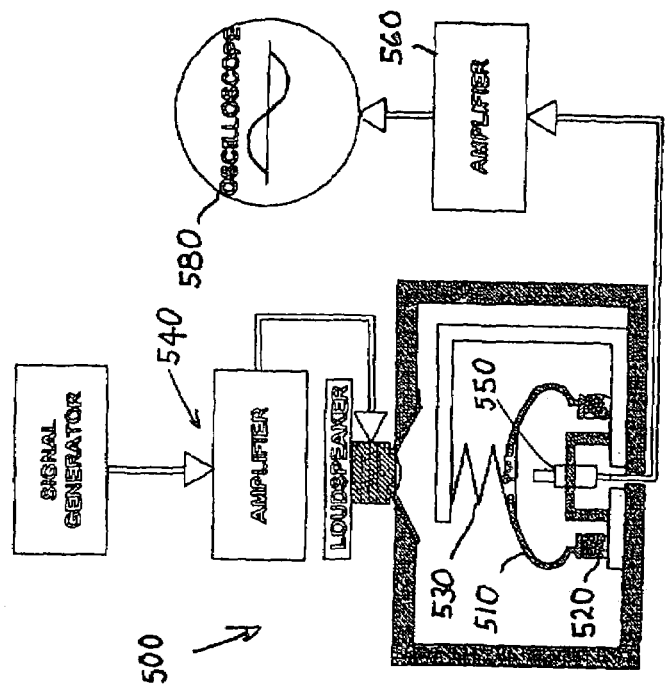
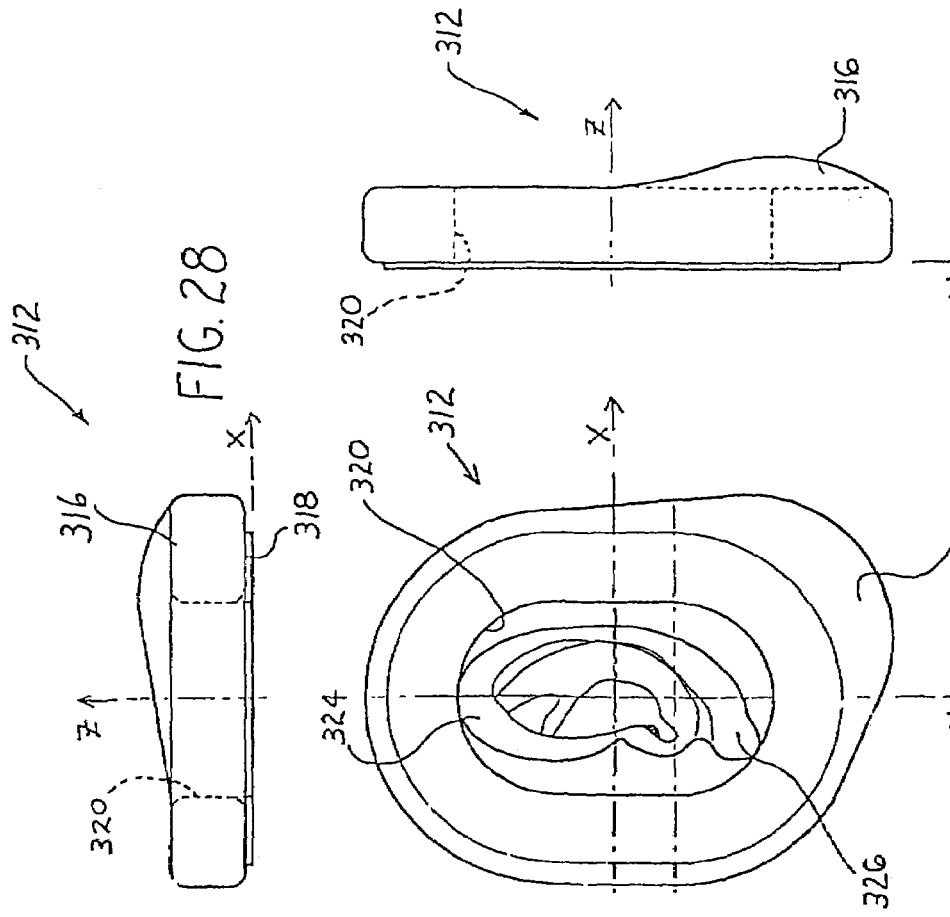

NOISE BARRIER APPARATUS HAVING ACOUSTIC WAVE DAMPING CUSHIONS

CROSS-REFERENCE

This is a continuation-in-part of application Ser. No. 09/340,813, filed Jun. 28, 1999, now abandoned (which is a continuation of application Ser. No. 08/803,674, filed Feb. 21, 1997, now U.S. Pat. No. 5,917,918, which claims the benefit of U.S. Provisional Application No. 60/012,168, filed Feb. 23, 1996), and of application Ser. No. 09/129,797, filed Aug. 6, 1998 (which claims the benefit of U.S. Provisional Application No. 60/055,395, filed Aug. 6, 1997).

Applicant's previous application Ser. No. 09/340,813, filed Jun. 28, 1999, and Ser. No. 09/129,797, filed Aug. 6, 1998, are hereby incorporated by reference in their entirety.

BACKGROUND OF THE INVENTION

The present invention was made with U.S. Government support, and the U.S. Government has certain rights in the invention.

The present invention relates to noise barrier apparatus for human ears and, more particularly, to in-ear noise barrier apparatus and over-the-ear noise barrier apparatus. The inventive apparatus may be used with or without integrated audio receivers. A particular aspect of the invention relates to an improved audio receiver which is fitted to a user's ear and which may be used in conjunction with an electronic stethoscope or other listening device such as a headset or similar device. The present invention may also be used with a typical, mechanical stethoscope or may be used as an ambient noise reducing ear plug.

Typical, mechanical stethoscopes comprise a stethoscope head and a pair of ear tubes that are coupled to the stethoscope head and biased together by a spring mechanism. Ear pieces or tips are mounted to the ends of the ear tubes for insertion into the user's ears. A column of air in the ear tubes transmits sounds detected by the stethoscope head to the ear pieces. The spring mechanism helps hold the ear pieces positioned in the user's ears. An electronic stethoscope may also have a speaker (i.e. earphone) or other electronic device in or next to the ear piece to assist in listening.

How the earpiece fits in the user's ear can affect both the comfort of the user and the overall effectiveness of the earpiece, i.e., the ability of the user to hear the sounds broadcast by the earpiece. FIG. 1 illustrates various parts of a human ear 10 and particularly shows the complex shape of the outer ear. The external or outer ear includes: the helix 12, a curved fold forming most of the rim of the external ear; the antihelix ridge 14, the inward curving ridge of the auricle (projecting outer portion) of the external ear; the triangular fossa or depression 16 between the antihelix 14 and the helix 12; the concha region 18, the larger depression near the opening into the ear canal; the ear lobe 20, the soft, pendulous, lower part of the external ear; the tragus 22, the fleshy prominence at the front of the external opening of the ear; the antitragus 24, the fleshy prominence opposite the tragus 22; the iscisua or notch 26 between the tragus 22 and antitragus 24; and the rim of or entrance 28 to the ear canal 30. The ear canal 30 provides a passageway between the external ear and the tympanic membrane or ear drum 32. Part of the jaw line interface 34 is shown extending downward from the ear 10.

It is generally desirable for the ear pieces to be biased or pressed against the user's ear so that a substantially airtight seal is formed. A good seal may prevent a significant amount of the ambient sounds or noise from reaching the user's ear drum via the ear canal through the entrance 28 to the ear canal and interfering with the stethoscope sounds. Achieving such an airtight seal, however, can be difficult and cause considerable discomfort to the user due to the relative hardness and shape of the ear pieces.

Typical earpieces for stethoscopes have a generally ball-like configuration that does not conform well to the complex shape of the human ear. In addition, the earpieces are often made from a relatively hard plastic material. When the earpiece is placed in the user's ear, it contacts and applies a force against a small area around the rim of or entrance 28 to the ear canal 30. The entrance 28 to the ear canal 30, however, can be particularly sensitive to pressure. The combination of a small contact area and the spring force from the spring mechanism of the ear tubes, therefore, oftentimes causes pain and discomfort to the user after a relatively short period of time. Furthermore, due to their bulbous configuration, the typical earpieces do not generally form a good seal with the ear and, therefore, do not serve well to reduce the amount of noise entering the user's ear canal 30 through the entrance 28.

The problems discussed above in connection with in-ear noise-barrier apparatus also apply to over-the-ear noise barrier apparatus.

In addition to not providing a very effective noise seal, prior art noise barrier apparatus also do very little to dampen and may even increase noise due to vibration of the noise barrier apparatus that may be transmitted through the earpiece structure to the user's ear. When an earpiece is subjected to an oscillating force, e.g. an external acoustic pressure wave (such as noise), the earpiece structure will react or respond to the oscillating force in a predictable vibrating manner which results in noise being generated on the internal side of the earpiece (as opposed to leaking past the earpiece) to the user's eardrum.

The oscillating response of an earpiece to an oscillating force is similar to the operation of an electromagnetic voice-coil in a conventional loud speaker. The voice-coil oscillates in response to an electrical signal at the coil and causes the speaker cone to vibrate and generate an acoustic pressure wave that results in sound. Similarly, an earpiece will oscillate or vibrate in response to a time varying force such as noise resulting in the generation of an acoustic pressure wave at the tip of the earpiece. This oscillation or vibration of the earpiece is analogous to the undamped or insufficiently damped oscillation of a linear spring-mass system. The acoustic pressure wave is then transmitted along the user's ear canal to the eardrum. As a result, unwanted noise is thereby transmitted to the user's ear.

Prior art cushions provided on both in-ear and over-the-ear noise barrier apparatus, are typically formed of materials, such as foamed polyurethane, that are elastically deformable such that, although they deform when a force is applied thereto, they quickly rebound to their original shape once the force is removed. While these cushions are soft, compliant, and are considered by most users to be reasonably comfortable, they perform other functions poorly. Most importantly, such elastically deformable materials act like linear springs such that, once acted upon by external acoustic waves, they will oscillate so as to essentially conduct or propagate the external wave through the cushion material. This oscillation of the cushion material causes acoustic waves to be generated within the audio chamber of the noise barrier device (including the ear canal itself), thus generating considerable noise and pressure incident in the ear canal.

SUMMARY OF THE INVENTION

An object of the present invention, therefore, is to provide an improved noise barrier apparatus which is comfortable, develops high levels of mechanical damping to inhibit generation of sound waves internally of the earpiece structure due to presence of sound waves or other pressure waves externally of the earpiece structure, and creates a good acoustic seal to prevent leakage of noise past the earpiece structure. The present invention noise barrier apparatus is preferably composed of material, and has a configuration, which suppresses the tendency present in state-of-the-art ear pieces to oscillate in response to a variable pressure wave, e.g., an acoustic pressure wave. Accordingly, the present invention is able both to prevent noise from leaking-past the earpiece structure and entering the ear canal and to suppress (dampen) noise from being generated at the earpiece structure and transmitted to the user's ear canal.

Furthermore, according to an aspect of the present invention, an ear piece safely houses a speaker which is directed into the user's ear canal. Thus, a preferred embodiment of the present invention provides an in-ear-canal audio receiver comprising an in-ear-canal adapter body having a tapered ear plug portion that is inserted into the user's ear canal. The adapter body further has an opening in the plug portion, an exterior annular indent, and an inner chamber coupled to the opening of the plug portion. The inner chamber of the in-ear-canal adapter body holds a transducer assembly comprising a transducer housing and a transducer or speaker. The transducer is positioned in a passage extending through the transducer housing. A concha cushion is positioned on the plug portion of the in-ear-canal adapter body in the annular indent. The cushion provides comfort and establishes a good seal with the user's ear. The cushion can also be custom configured to match the complex shape (concha and ear canal region) of the user's outer ear. The custom shape provides both greater comfort and a better seal.

The transducer assembly further comprises a transducer adapter body having a through hole and an end cap which covers one end of the through hole. The transducer fits into the through hole of the transducer adapter body, and the transducer adapter body together with the transducer are received in the passage of the transducer housing. In another embodiment of the invention, a transducer is encapsulated in an encapsulating material such as an epoxy compound.

Thus, the present invention provides a noise barrier apparatus for preventing external noise from causing noise in ears on opposing sides of a user's head. The noise barrier apparatus comprises a pair of noise barrier devices to be held against the opposing sides of the user's head at the respective ears, and a noising barrier device holding apparatus coupled to the noise barrier devices to hold the noise barrier devices against the opposing sides of the user's head at the respective ears. The noise barrier devices respectively comprise audio chamber defining parts constructed to define enclosed audio chambers including the ear canals of the ears. The audio chamber defining parts respectively include cushion interface parts to bear against the opposing sides of the user's head, and these cushion interface parts respectively comprise peripherally extending cushions to encircle the ear canal entrances of the ears. The peripherally extending cushions are deformable so as to be conformable to the opposing sides of the user's head at areas surrounding the ear canal entrances, respectively, when the audio chamber defining parts are held thereagainst by the noise barrier device holding apparatus. Each of the peripherally extending cushions comprises a material which is at least partially plastically deformable. Preferably, each of the peripherally extending cushions comprises a material providing a damping ratio ($C/C_c$) greater than 0.75 so as to attenuate (rather than amplify) the magnitude of external acoustic waves as conducted by the noise barrier apparatus into the audio chambers which includes the ear canals of the ears. More preferably, the material of each of the peripherally extending cushions provides a damping ratio of greater than or equal to 1.0

The present invention also contemplates a noise barrier apparatus for preventing external noise from causing noise in an ear on a side of the user's head, wherein the noise barrier apparatus comprises: a noise barrier device to be held against the side of the user's head at the ear. The noise barrier device comprises an audio chamber defining part constructed to define an enclosed audio chamber including the ear canal of the ear when the noise barrier devices are held against the side of the user's head at the ear. The audio chamber defining part includes a cushion interface part to bear against the side of the user's head, and the cushion interface part comprises a peripherally extending cushion to encircle the ear canal entrance of the ear. The peripherally extending cushion is deformable so as to be conformable to the side of the user's head at an area surrounding the ear canal entrance when the audio chamber defining part is held thereagainst. The peripherally extending cushion comprises a material which is at least partially plastically deformable, and which provides a damping ratio greater than 0.75 and, more preferably, greater than or equal to 1.0.

As referred to in the present application, the term "plastically deformable" refers to a material which deforms upon application of a force thereto and does not return to its original shape once the force is removed. The term "partially plastically deformable" refers to a material that deforms upon application of a force thereto and does not immediately return to its original shape (in the sense that an elastically deformable material does) but will slowly return fully or partially to its original shape. The term "at least partially plastically deformable" refers to a material that is either "plastically deformable" or "partially plastically deformable."

The present invention also provides a stethoscope equipped with an in-ear-canal receiver as described above. The present invention also provides an ear plug having a concha cushion.

According to another preferred form of the invention, an over-the-ear noise barrier apparatus includes ear cups and audio seal cushions which surround the user's ears. The cushions conform to the shape of the user's head area surrounding the ears so as to form excellent audio seals, and are formed of material having a high damping characteristic to suppress conduction of external pressure waves (e.g. sound waves) to the interior of the ear cups. The material is at least partially plastically deformable and provides a damping ratio greater than 0.75 and, preferably, greater than or equal to 1.0.

It is contemplated that the noise barrier apparatus of the present invention can be constituted by a combination of the over-the-ear noise barrier devices and in-ear noise barrier devices, wherein both an in-ear device and an over-the-ear device are provided for each ear.

It is further contemplated that the noise barrier apparatus of the present invention can be constituted with audio seal cushions formed of plural, concentric concha cushions, and that the concha cushions can be formed of either the same or different material.

BRIEF DESCRIPTION OF THE DRAWINGS

The above and other objects and advantages of the invention will become apparent from consideration of the following detailed description when read in conjunction with the accompanying drawings, in which like reference characters refer to like parts throughout, and in which:

FIG. 5 is a partial, side cross-sectional view of an earpiece assembly comprising the in-ear-canal ("IEC") adapter and the ear cushion, which form a part of the IECR of FIG. 3;

FIG. 6A is an end view of an ear cushion forming a portion of the IECR of FIG. 3;

FIG. 6B is a side view of the ear cushion of FIG. 6A;

FIG. 6C is a side cross-sectional view of the ear cushion of FIG. 6A;

FIG. 7 is a side view of an in-ear-canal ("IEC") adapter forming a portion of the IECR of FIG. 3;

FIG. 8A is another side view of the IEC adapter illustrating the interior contour;

FIG. 8B is an end view of the IEC adapter of FIG. 6A;

FIG. 9A is a side cross-sectional view of an end cap for a transducer adapter body (shown in FIG. 10);

FIG. 9B is an end view of the end cap of FIG. 19A;

FIG. 10 is a side cross-sectional view of an encapsulated transducer assembly comprising the end cap and a transducer positioned in a transducer adapter body, which form a part of the IECR of FIG. 3;

FIG. 11A is a side cross-sectional view of the transducer positioned in the transducer adapter body of FIG. 10;

FIG. 11B is an end view of the transducer positioned in the transducer adapter body of FIG. 11A; and FIG. 11C is an opposing end view of the transducer positioned in the transducer adapter body of FIG. 11A;

FIG. 11D is a cross-sectional plan view of the transducer positioned in the transducer adapter body of FIG. 11A;

FIG. 12A is an exploded, side cross-sectional view of another embodiment of an encapsulated transducer assembly and transducer housing;

FIG. 12B is a side cross-sectional view of the encapsulated transducer assembly of FIG. 12B partially inserted into the transducer housing;

FIG. 12C is a side cross-sectional view of the encapsulated transducer assembly of FIG. 12A fully inserted in the transducer housing and the transducer housing mounted to the end of a stethoscope ear tube;

FIGS. 27–29 are views showing the construction of a circumaural cushion of the apparatus of FIGS. 25 and 26; and FIG. 30 schematically illustrates a test arrangement for determining oscillatory decay of a noise barrier apparatus.

The terms "upward", "downward", "top", and "bottom" may appear in the following description for convenience in describing the invention. The use of these or like terms are not intended to limit the orientation of the invention.

DETAILED DESCRIPTION OF THE INVENTION

A first embodiment of the present invention provides an in-ear-canal audio receiver (hereinafter referred to as an "IECR") that may be used with an electronic stethoscope, or other electronic listening device such as a headset, for receiving sound signals and broadcasting sounds into the ear canal of a user. The IECR of the present invention is designed to comfortably fit in the user's ear and yet provide a good acoustic seal against external noise. As discussed further below, the IECR may also be used with a more conventional, mechanical stethoscope which uses a column of air in the ear tube to transmit sounds to the IECR. Or, the IECR may be used as a comfortable ear plug for passively reducing the amount of ambient noise reaching the inside of a user's ear 10.

Figure 1:
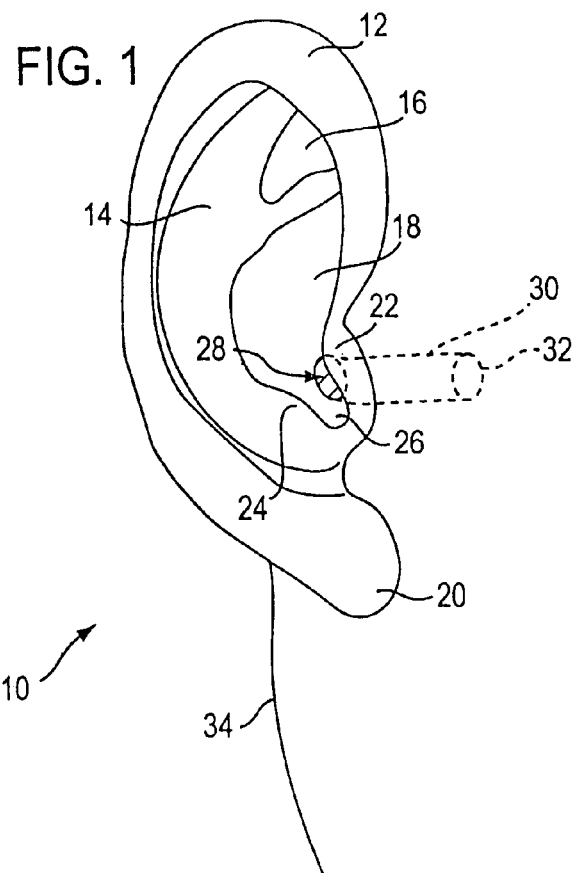
FIG. 1 is a side view of a human ear illustrating the various parts of the ear.
Figure 2:
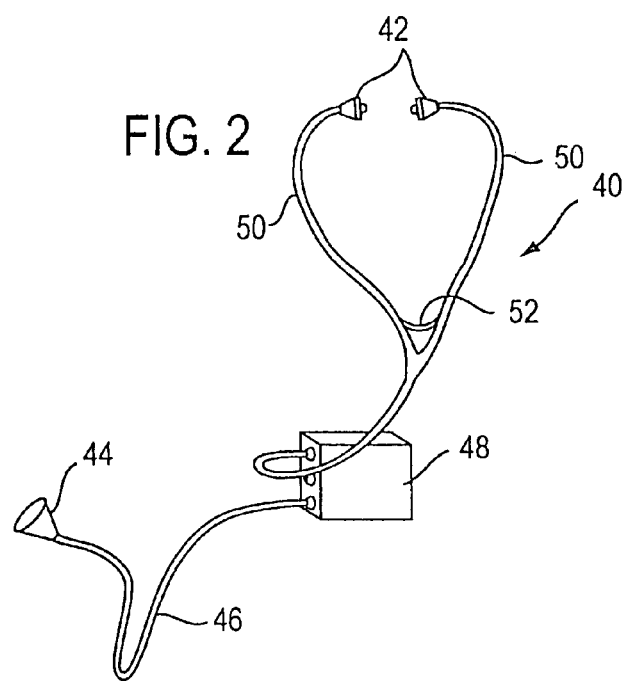
FIG. 2 is a perspective view of an electronic stethoscope equipped with an in-ear-canal audio receiver (herein "IECR") in accordance with the present invention.

An example of an electronic stethoscope is described in U.S. Pat. No. 5,467,775, issued Nov. 21, 1995 to Thomas F. Callahan and Matthew G. Callahan, which is incorporated herein by reference. FIG. 2 illustrates the electronic stethoscope 40 of the '775 patent provided with two IECRs 42 in accordance with the present invention. The electronic stethoscope 40 includes two transducers (not shown) housed in a stethoscope head 44 for detecting body sounds of a patient. The sound signals are transmitted by conductors housed in a cable 46 to a digital signal processor (not shown) carried in a pack 48 or similar container or box. The digital signal processor processes the sound signals, and conductors, housed in a pair of calipers, or ear tubes 50, carry the processed sound signals to the IECRs 42 mounted to the ends of the ear tubes 50. The IECRs 42 then broadcast the sounds to the user's inner ear. A spring mechanism 52 biases the calipers 50 together in order to hold the IECRs 42 more securely in the user's ears.

Figure 3:
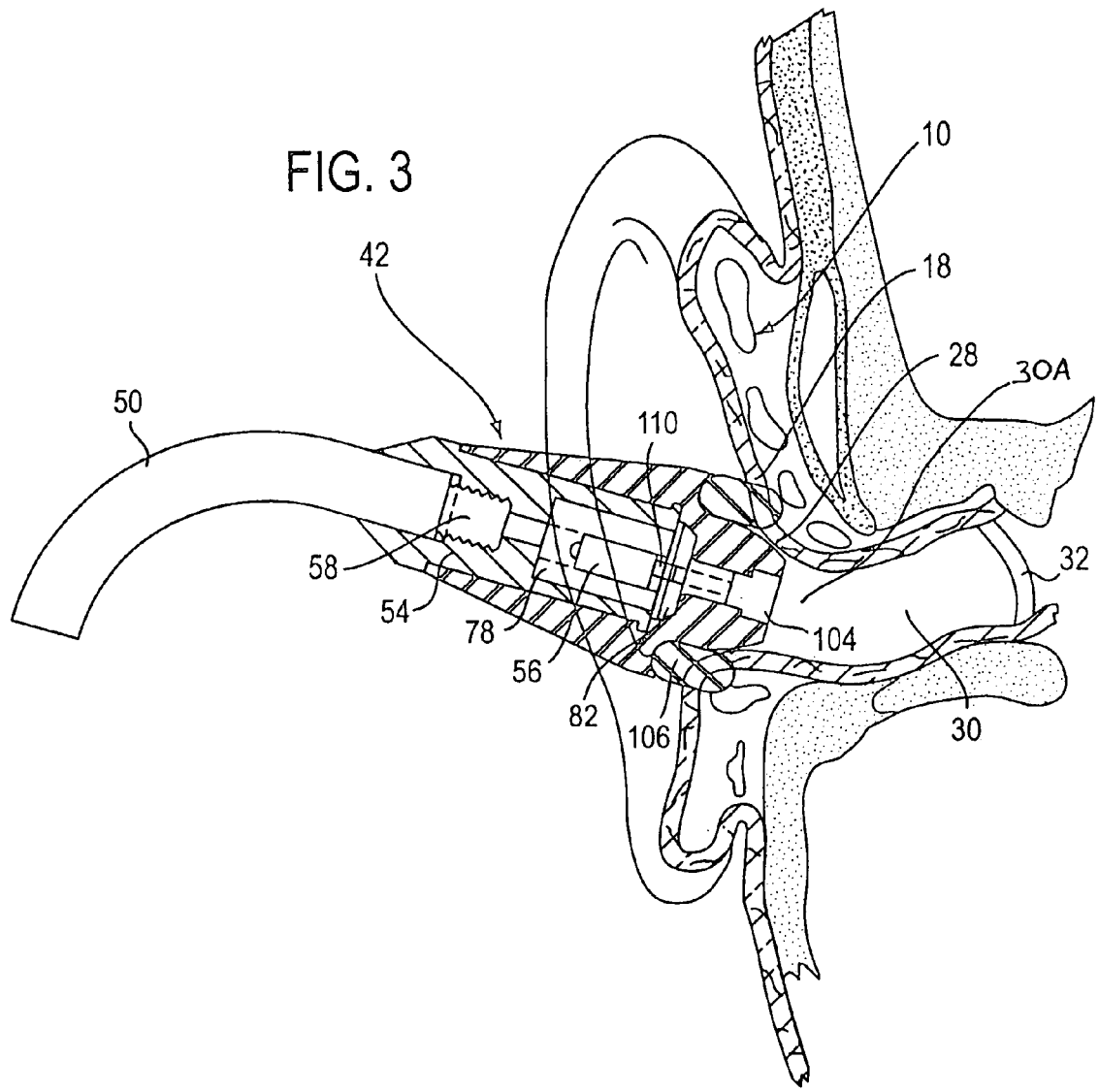
FIG. 3 is a side cross-sectional view of the IECR positioned in a human ear.
Figure 4:
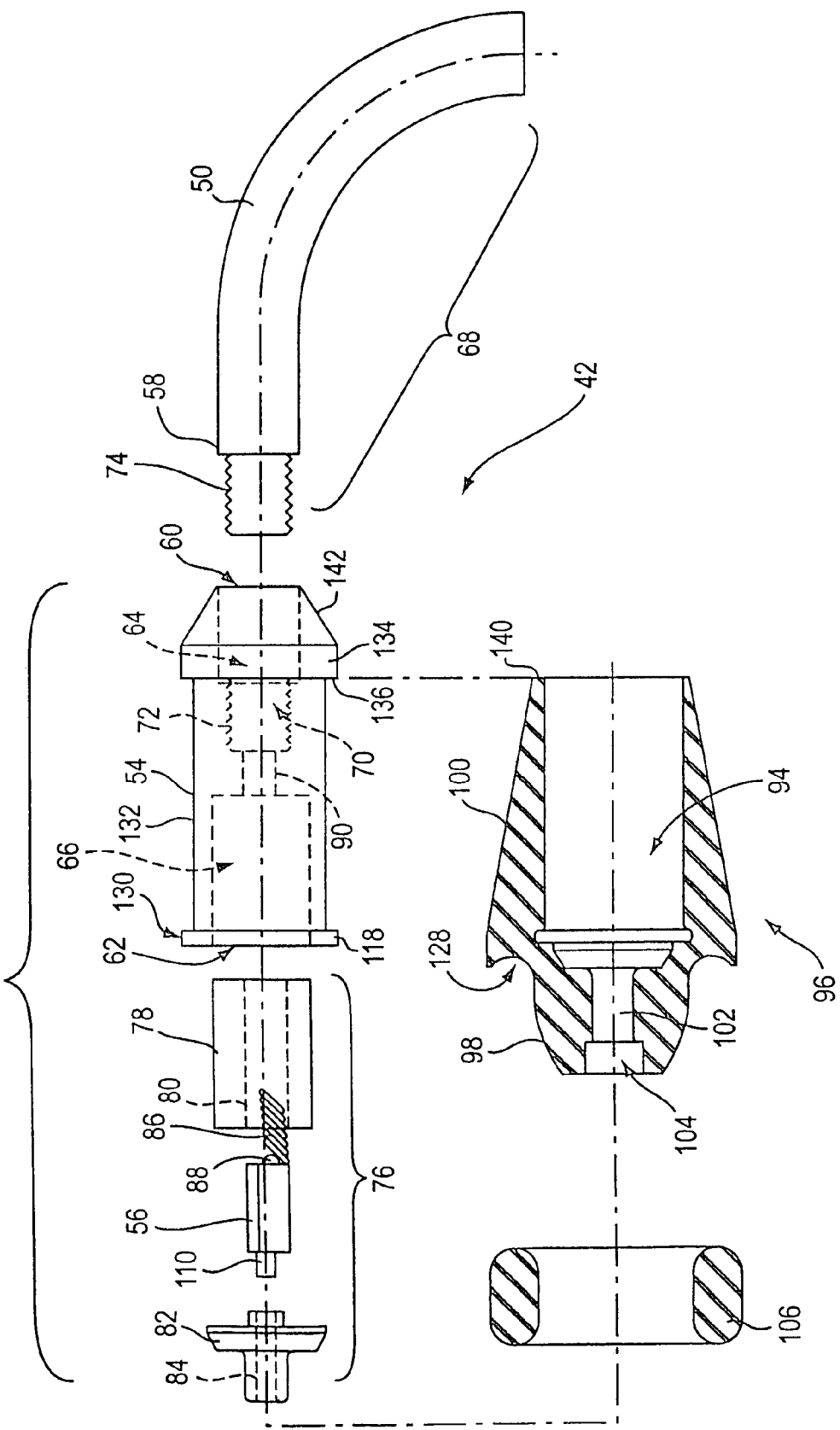
FIG. 4 is an exploded side view of the IECR of FIG. 3.

FIG. 3 illustrates a first embodiment of an in-ear-canal receiver ("IECR") 42 positioned so that a portion of the IECR projects into the ear canal 30 of a human ear 10. With reference to FIGS. 3 and 4, the IECR 42 comprises a transducer housing 54 which holds a transducer 56 and which may be attached directly to the end 58 of a stethoscope ear tube 50. The transducer housing 54 has openings 60, 62 on either end which open into first and second chambers 64, 66, respectively. The first chamber 64 is adapted to be mounted to the end 58 of the stethoscope ear tube 50 which is typically hollow and made from a metallic material along a distal section 68 (shown in FIG. 4). The first chamber 64 includes a subchamber 70 provided with threads 72 for engaging threads 74 provided on the end 58 of the stethoscope ear tube 50.

Figure 19:
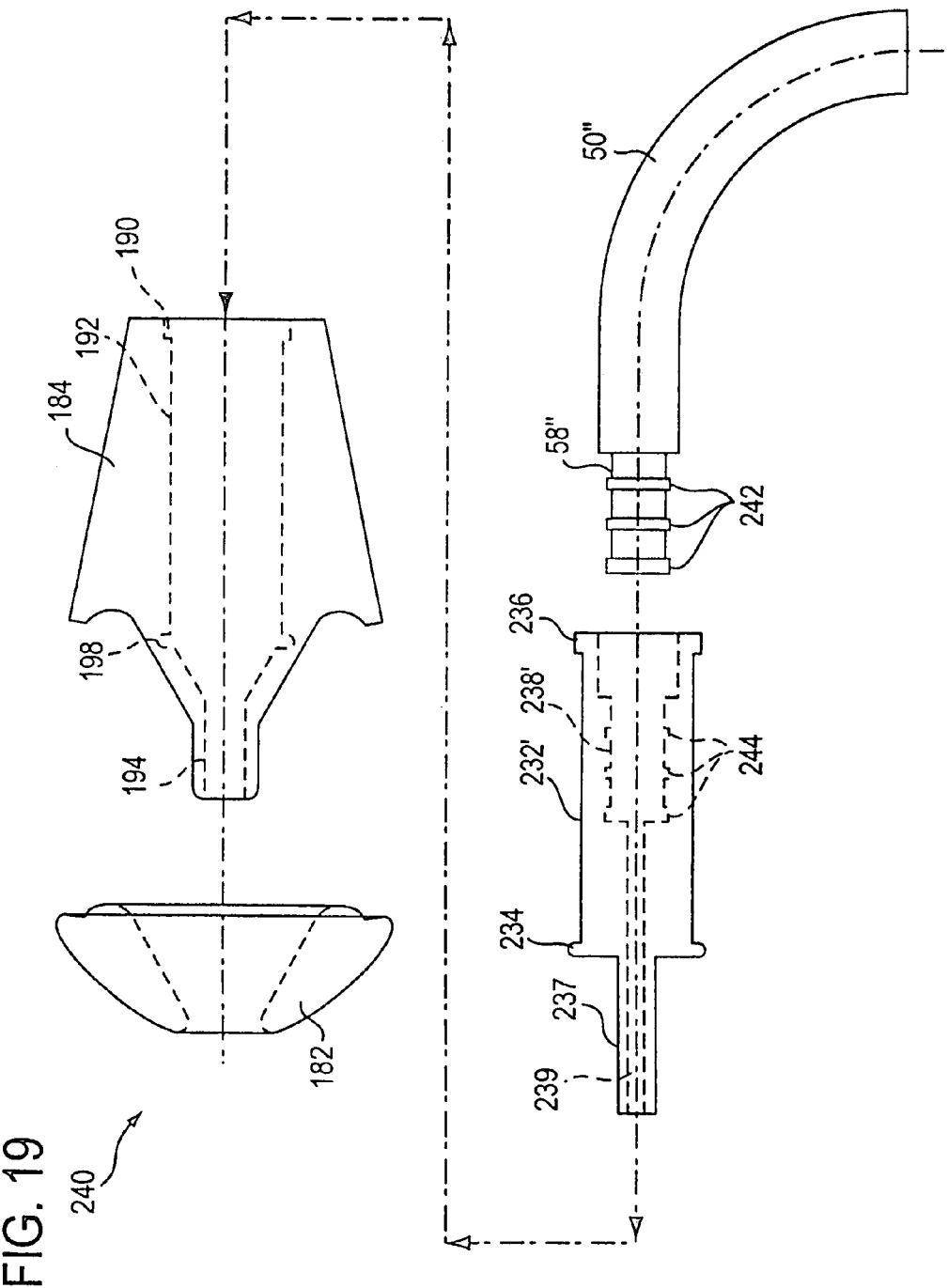
FIG. 19 is an exploded side view of another embodiment of an IECR similar to the IECR of FIG. 18 but with a different mounting configuration.

The configuration of the first chamber 64, however, may be modified to adapt to different terminal configurations of the stethoscope ear tube 50. For example, the end of the stethoscope ear tube may be provided with annular ridges that are press fit into corresponding annular indents provided inside the earpiece. FIG. 19, discussed in more detail further below, illustrates such a mounting arrangement between the housing and the end of the stethoscope.

The second chamber 66 of the transducer housing 54 is adapted to receive an encapsulated transducer assembly 76 that encloses the transducer 56. The encapsulated transducer assembly 76 comprises: a transducer adapter body 78, having a through hole 80 for receiving the transducer 56; an end cap 82, having a central through hole 84, for assisting in holding the transducer 56 within the transducer adapter body 78; the transducer 56; and a pair of conductor wires or leads 86 (shown in FIG. 4). The end cap 82 may be connected to the transducer 56 and the transducer adapter body 78 by an adhesive such as acrylic cement. The conductor wires 86 are preferably hard wired or soldered to contact points 88 provided at one end of the transducer 56 and are fed through the hollow ear tube 50 to the electronics pack 48. A passageway 90 connects the two chambers 64, 66 of the transducer housing 54 to allow passage of the electrical conductors 86 between the transducer 56 and the ear tube 50.

The entire transducer assembly 92 (i.e., transducer housing 54 and encapsulated transducer assembly 76) fits into a relatively large, open-ended, chamber 94 of an in-ear-canal adapter 96 (herein "IEC adapter"). The transducer assembly 92 may be held in place by an adhesive such as acrylic cement. Alternatively, the transducer assembly 92 may be press fit into the IEC adapter chamber 94 so that the IEC adapter 96 and transducer assembly 92 may be easily separated for replacement or repair. The IEC adapter 96 has a tapered plug section 98 that is inserted into the user's ear canal 30 and a larger adapter section 100 that holds the transducer assembly 92. The chamber 94 is shown in the adapter section 100, and a circular passageway 102 that extends through the plug section 98 connects the chamber 94 to an opening 104 in the plug section 98.

A toroid cushion 106 encircles the plug section 98 of the IEC adapter 96. The IEC adapter 96 and torus-shaped cushion 106 together form an earpiece assembly 108 (FIG. 5) which is inserted into the user's ear 10. In addition to providing comfort, the torus-shaped cushion 106 forms a good seal with the concha and ear canal region (18, 28) when the IEC adapter 96 is inserted into the ear 10. As discussed further below, the cushion is formed from material that both helps create a good seal and helps dampen or suppress the propagation of external noise vibrations via the earpiece structure to an audio chamber 30A defined by the IECR and the ear canal 30.

Due to the spring-biasing of the stethoscope calipers 50, the IECR 42 is urged toward and into the user's ear canal 30 as shown in FIG. 3. As the IECR 42 is urged into the ear canal 30, the toroid cushion 106 is compressed against the concha and entrance (18, 28) to the ear canal 30 forming a seal. The plug section 98 of the IEC adapter 96 is urged into the ear canal 30 and also forms a good seal with the concha/ear canal 30 (18, 28).

When the IECR 42 is so positioned in the ear 10, the audio output 110 of the transducer 56 is directed into the ear canal. Depending upon the size of the transducer 56 and the encapsulated transducer assembly 76, however, the encapsulated transducer assembly 76 may be fit into the plug section 98 of the IEC adapter 96 instead of the adapter section 100. In other words, a chamber may be formed in the plug section 98 for receiving the encapsulated transducer assembly 76. In that way the transducer 56 may be brought even closer to the ear drum 32 when the IECR is positioned in the user's ear 10.

FIGS. 5, 6A–C, 7, 8A, 8B, 9A, 9B, 10, and 11A–D illustrate in detail the configurations of the components of the IECR 42. Although the following detailed discussion of the components mentions particular dimensions, the dimensions may be modified depending upon such variables as the transducer size and size of the intended user's ear. For example, where the user's ear is relatively small or large, the cushion 106 can be made correspondingly smaller or larger, and where the transducer is relatively small or large, the encapsulating assembly 76, transducer housing 54, and IEC adapter 96 can be made correspondingly smaller or larger.

FIG. 5 partially shows the earpiece assembly 108 (IEC adapter 96 and toroid ear cushion 106) fully assembled with the torus-shaped cushion 106 positioned on the plug section 98 of the IEC adapter 96. As shown in FIGS. 6A–C, the torus-shaped cushion 106 has a circular or "donut" shape with a generally flattened, elliptical cross-section (FIG. 6C). In the embodiment illustrated, the toroid ear cushion 106 has inner and outer diameters of 0.429 inches ("in.") (1.09 centimeters ("cm")) and 0.6875 in. (1.746 cm.), respectively, and is 0.130 in. (0.33 cm.) thick. The cushion 106, however, can be larger to provide an even greater contact area between the cushion 106 and the user's ear 10, as discussed further below.

The ear cushion may also be custom configured to match the complex shape (concha and ear canal region (18, 28)) of the user's outer ear. For example, the cushion may be larger and more flattened on the side which presses against the user's ear in the concha region to provide a greater area of contact between the cushion and the user's ear. The custom shape provides both greater comfort and a better seal. FIGS. 13, and 16A–D, discussed further below, illustrate an ear cushion that is more custom configured to conform to the shape of the user's ear.

The ear cushion 106 is preferably formed of a material that is deformable so as to conform to the area at the side of the user's head against which the cushion bears when in use and, in particular, so as to conform to the portion (e.g. the concha region) directly surrounding the opening to the ear canal 30 (See FIG. 3) in the present embodiment in-ear noise barrier apparatus. Such a deformable material provides for a high sealing characteristic for sealing against external noise leaking past the cushion and into the audio chamber 30A defined by the noise barrier device and the ear canal 30.

The material of the cushion 106 should also be such as to provide high mechanical damping so that external acoustic pressure waves are not readily propagated through the noise barrier device and into the audio chamber 30A (i.e. so that oscillations (vibrations) of the noise barrier device itself due to external acoustic pressure waves are attenuated or dampened) so as to greatly reduce acoustic pressure waves in the audio chamber 30A. To this end, the ear cushions 106 are preferably formed of a material that is at least partially plastically deformable and preferably has a damping ratio greater than 0.75 and, more preferably, greater than or equal to 1.0.

The cushion 106 may comprise a highly flexible (perhaps elastically deformable) sheath filled with silicon gel or another soft material such as a moldable putty. The flexible sheath may comprise a wear resistant thin, film-like material, such as polyvinyl chloride (PVC), polyvinyl chloride-acetate, polyurethane, or kid skin leather, and be filled with a silicon gel, gel mixture or moldable putty, e.g., a high viscosity silicon liquid (or gel) that is highly filled with clay (for example, SILLY PUTTY™) or an admixture of clay and glass or plastic micro-spheres. The cushion may also be formed of a slow recovery foam that is partially plastically deformable. In general, the moldable material can be compounded so that it will retain its amorphous qualities and take the shape of the concha cavity in which it is compressed, at least during use. Such material tends to gradually flow under slight pressure and body heat. Other materials (e.g. putty) can be compounded to take a permanent set so that once deformed to the shape of the user's concha, the cushion 106 will tend to retain its shape after prolonged exposure to body heat. The cushion 106 may also comprise of another very soft moldable material (e.g. wax).

Thus, in a preferred form of the invention, the cushion may comprise a viscoelastic material and/or a highly viscous or plastic material, such as soft clay, putty, or dough, or a partially plastically deformable material such as slow recovery form. As discussed below, these materials develop an actual damping coefficient (C) that is greater than a theoretical critical damping coefficient ($C_c$) for the system, which results in a damping of noise vibrations.

As used herein, the term "plastically deformable" refers to a material which deforms upon application of a force thereto and does not return to its original shape once the force is removed. The term "partially plastically deformable" refers to a material that deforms upon application of a force thereto and does not immediately return to its original shape (in the sense that an elastically deformable material does) but will slowly return fully or partially to its original shape. The term "at least partially plastically deformable" refers to a material that is either "plastically deformable" or "partially plastically deformable."

As noted above, the cushion may be formed of an "at least partially plastically deformable" material, either alone or enclosed in a sheath which may or may not be elastically deformable.

Figure 21:
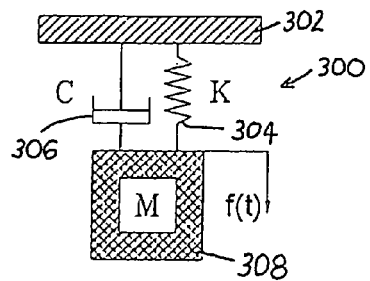
FIG. 21 is a schematic of a linear spring-mass system with viscous damping.

The earplug response to an oscillating force such as an acoustic pressure wave (sound) is analogous to the response of a classical spring-mass system subjected to an oscillating force such as an acoustic pressure wave. With reference to FIG. 21, classical spring-mass system 300 is composed of the following four elements:

(1) A rigid immovable base (or reference plane) 302.

(2) A linear spring 304 with a spring stiffness coefficient (K) that may be expressed in units of pounds (lbs.) per inch (in.) of deflection or motion. This is also referred to as a linear restoring force.

(3) A damping device 306 with a damping coefficient (C) that may be expressed in units of pounds-seconds (lbs.-sec.) per inch (in.).

(4) A mass (M) 308 that may be expressed in units of (lbs.)(sec$^2$/in.).

A forcing function f(t) is interpreted to be any force that increases or decreases as a function of time, e.g. (F)(sinωt). The classical spring-mass system of FIG. 21 can be represented mathematically by a linear ordinary differential equation:

$$M(d^2x/dt)+C(dx/dt)+Kx=f(t) \qquad \text{(Equation 1)}$$

where x is the displacement of the mass, dx/dt is the velocity of the mass, and d$^2$x/dt is the acceleration of the mass.

In order to more clearly understand the above equation, it can be helpful to examine the characteristics normally associated with a linear spring. For example, if the damping coefficient C is assumed to be zero (0), then the above equation (Equation 1) reduces to:

$$M(d^2x/dt)+Kx=f(t) \qquad \text{(Equation 2)}$$

Figure 22:
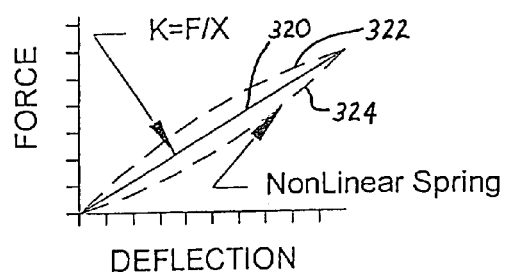
FIG. 22 is a graph of a force-deflection curve for a linear elastic spring.

Accordingly, if the mass M (308) is displaced from equilibrium by a force f(t), the only restoring force comes from the linear elastic spring (304). With reference to FIG. 22, the linear elastic spring has constant physical characteristics that can be illustrated by a force deflection curve (straight line, 320). When an external force f(t) is applied to a linear elastic spring and causes the spring to deflect (stretch), the spring reacts and provides a restoring force that is equal and opposite to the applied force f(t).

This physical law governs the response of many materials and configurations subjected to an external force. For example, this law largely governs the response of an elastomer (rubber) tip on the traditional stethoscope earpiece or the silicone rubber earplug when subjected to an external pressure wave such as a noise wave. For this system, the natural frequency $\omega_n$ in radians per second is defined by:

$$\omega_n=(K/M)^{1/2} \qquad \text{(Equation 3)}$$

or the natural frequency $f_n$ in cycles per second or Hertz (Hz) may be defined by:

$$f_n=\tfrac{1}{2}\pi(K/M)^{1/2} \qquad \text{(Equation 4)}$$

When a force is applied and then quickly removed from such a system, the system will vibrate at its natural frequency until friction or some other form of damping gradually absorbs the energy and the system eventually comes to rest.

FIG. 22 also includes a second, dashed curve which illustrates a typical nonlinear spring characteristic. As an increasing force is applied, the deflection follows the upper curved dashed line 322. As the force is decreased, the spring recovers its initial position by following the lower curved dashed line 324. The area enclosed by the two dashed lines represents lost energy, usually in the form of a hysteresis loss (internal molecular level heat) which is actually another form of natural damping. While hysteresis and friction damping are present in most mechanical systems, they are usually neglected in computations when the damping coefficients are small.

An important physical characteristic apparent from equations 3 and 4 above is the spring stiffness (K) of the system. The spring returns the system to its initial condition when the unbalanced force is removed. In a practical sense, this is an important feature of the dynamic system because by measuring the deflection under the action of a known load, the natural frequency can be readily determined.

From the spring stiffness K, the theoretical or critical damping coefficient ($C_c$) of the system can be determined:

$$C_c = 2(KM)^{1/2} \qquad \text{(Equation 5)}$$

In a dynamic system, the relationship between the actual damping coefficient (C) and the critical damping coefficient ($C_c$) can provide another important physical characteristic. This relationship can be expressed as a damping ratio $\beta (=C/C_c)$.

Figure 23:
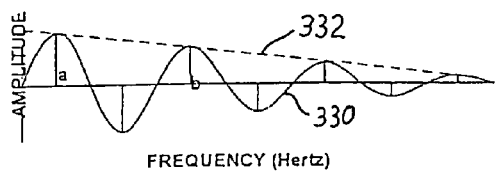
FIG. 23 is a plot showing oscillatory decay over time of a noise barrier device.

The system's damping coefficient ($C_c$) can also be determined by exciting the system and measuring the time taken for the oscillation to decay to zero (See FIG. 23). The decaying vibration is illustrated in FIG. 23 by the solid curved line 330. The dashed line 332 that envelopes the decaying vibration is known as the "Logarithmic Decrement" ($\Delta$). The Logarithmic Decrement ($\Delta$) can be approximated by measuring the amplitude of the decaying vibration at two consecutive peaks (e.g. a and b, FIG. 23) on an oscilloscope, for example, and taking the logarithm of the ratio.

In particular, $$\text{the logarithmic decrement } \Delta = \ln(a/b) = 2\pi\beta(1-\beta^2)^{-1/2} \qquad \text{(Equation 6)}$$

This equation can be approximated as:

$$\Delta = \ln(a/b) = 2\pi\beta \qquad \text{(Equation 7)}$$

Thus, since $\beta = C/C_c$, $$\beta = C/C_c = [\ln(a/b)] \div (2\pi) \qquad \text{(Equation 8)}$$

Although testing arrangements for determining the logarithmic decrement of the oscillations (vibrations) of a system are known in the art, FIG. 30 illustrates a preferred testing system 500 for determining the logarithmic decrement (i.e. for determining the amplitudes a and b at successive peaks in a decaying vibration on an oscilloscope). FIG. 30 schematically illustrates a noise barrier device 510 having a cushion interface part 520, arranged with a spring 530 for representing the spring force applied to the noise barrier device 510 in the particular noise barrier apparatus (e.g. by the headband 362 in FIG. 26 or the spring mechanism 52 in FIG. 2). An oscillation drive arrangement 540 is provided for creating oscillations of the noise barrier device 510 having, for example, a small piece 570 of magnetic iron or steel attached to the inside center of the noise barrier device 510 (note that the weight of the magnetic iron or steel piece must not appreciably affect the system weight). A proximity transducer arrangement 550 is located a short distance from the iron or steel piece 570. The output signal from the transducer arrangement 550 can be amplified by an amplifier 560 and observed on an oscilloscope 580 or other recording device. The noise barrier device 510 is caused to oscillate freely until it stops due to its own mechanical damping. The decay in the oscillation will, for example, be observed on the oscilloscope 580 as illustrated in FIG. 23, and the amplitudes a and b of successive oscillation peaks can be measured. The value of the damping ratio $\beta$ can thus be calculated according to the equation 8 above. The oscillation unit 540 is preferably a loud speaker capable of reproducing pure tone signals input from the illustrated oscillator or preferably signal generator and power amplifier. The element 580 of FIG. 30 represents an oscilloscope or some other recording apparatus. The sound wave output from the driver unit causes the noise barrier device 510 to vibrate in the vertical mode.

Figure 26:
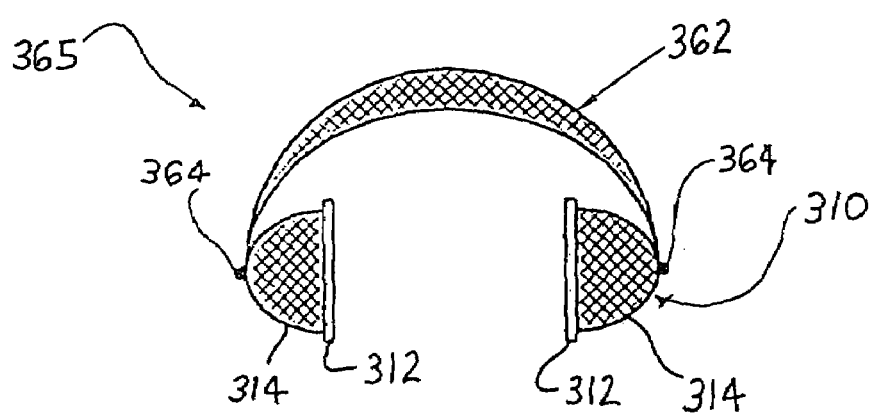
FIG. 26 is a front view of the overall noise barrier apparatus of FIG. 25.

It is noted that the schematic spring 530 shown in FIG. 30 represents the spring force provided to the individual noise barrier devices 510 by external spring forces, such as provided by the spring mechanism 52 of a stethoscope (see FIG. 2) or the ear cup bridge (head band) 362 coupling together the ear cup assemblies 310 of the head set 365 (see FIG. 26).

When this simple system is disturbed by a short duration pulse (shock load, for example), it will initially deflect in response to the load. However, when the load is removed, the system will vibrate at its natural frequency ($\omega_n$) for a period of time until friction or some other form of damping absorbs the energy and the system comes to rest (FIG. 23).

Figure 24:
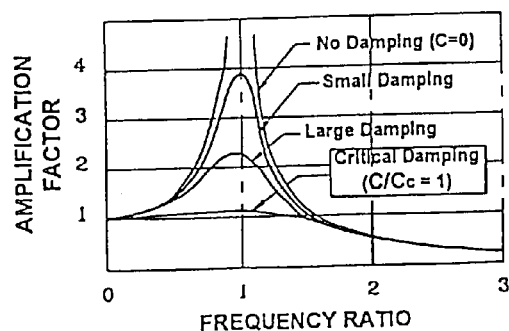
FIG. 24 is a graph of noise amplification factors plotted against the ratio of forcing frequency to natural frequency.

FIG. 24 shows a graph of the noise amplification factor plotted against the ratio of the forcing frequency ($\omega$) to the natural frequency ($\omega_n$) (ratio, $\omega/\omega_n$) for the simple dynamic system illustrated in FIG. 21. For a hypothetical situation where there is no damping ($C/C_C=0$), the amplification factor approaches infinity. However, in the real world all mechanical systems have some small amount of natural damping. If the system has a small damping ratio (e.g., $C/C_C=0.15$), the amplification factor is quite high, e.g., approaches 4. This means that the dynamic deflection is four times greater than the static deflection. When the external noise contains frequency components in a bandwidth that nearly matches the system's natural frequency, the noise components within that band are amplified to a level that is four times greater than the original input noise. The amplified noise is then transmitted along the ear canal to the eardrum. Under certain circumstances, this could lead to hearing impairment.

Even when the damping ratio is somewhat higher (e.g., $C/C_C=0.25$), the amplification factor is approximately 2. A preferred goal of the present invention, therefore, is to achieve a critical damping ratio that is greater than or equal to 1.0. (i.e., $C/C_C \geq 1$). To achieve this goal, the cushion 106 of the present invention preferably comprises a material or materials that allow the cushion to achieve an actual damping value C that is greater than or equal to the critical damping value $C_c = 2(KM)^{1/2}$; in other words, so that the damping ratio is greater than or equal to 1.

Materials and configurations currently used for earpieces (e.g. stethoscope ear tips) typically are either soft rubber, soft polyvinyl chloride (PVC) and sometimes polyethylene. These materials exhibit characteristics that are similar to a linear or slightly nonlinear spring with relatively small damping coefficients. The relatively low magnitude of the natural damping expected from rubber can be demonstrated by attaching one end of a rubber band to a rigid stationary platform (ceiling) with a weight attached to the other end. If the weight is then displaced from its static equilibrium position, released, and allowed to move freely; it will oscillate about its static equilibrium position for a considerable period of time before coming to rest. This type demonstration is clear evidence of the low level of the natural damping associated with a soft rubber ear-tip cushion used with most stethoscopes.

Cushion materials which are considered to provide the necessary mechanical damping (i.e. provide a system damping ratio $\beta=C/C_c>0.75$, and preferably greater than or equal to 1), include: silicone gel filled with micro-spheres; putty; clay; silicon gel highly fill with clay (such as SillyPutty™); lanolin (a highly viscous material, similar to a thick paste), wax, and slow recovery foam. Of course, some of the materials cannot hold their own shape, and thus, to be used in a cushion, would be required to be encased within a shell material such as leather, soft plastic, a polyvinyl chloride or polyurethane skin. Although slow recovery foam may be formed of polyurethane, it is formed by a known process which causes the material to not be elastically deformable, but to rather be partially plastically deformable.

It is also contemplated that the cushion of the present invention could be formed of multiple materials respectively constituting plural concentric rings. For example, such a cushion could include one ring formed of a material (e.g. putty) providing a very high mechanical damping ratio, and a second concentric ring being formed of a material having a lower damping ratio but with superior characteristics in other regards (e.g. ability to conform to the side of the user's head (either within or outside of the ear)) so as to provide an exceptional acoustic seal which, by conforming well to the side of the user's head, will avoid minute openings between the cushion and the user's head and thereby prevent leakage of sound waves into the internal audio chamber which includes the ear canal.

Although the currently preferred embodiments of the present invention utilize components (e.g. the transducer assembly 92 other than the cushion 106) formed of more brittle material (such as ABS plastic) with only the cushion part being formed of the material providing a high damping ratio, it is contemplated that all components or many of the components of the noise barrier device which define the audio chamber including the ear canal, may be formed of the cushion material (i.e. the material having the high damping ratio (e.g. greater than 0.75) and which are at least partially plastically deformable).

The materials known as "slow recovery foams" are considered to be nonlinear springs, i.e. when deformed they slowly return to their initial condition. These are examples of materials that are "partially plastically deformable."

There are two general classes of materials which, when combined with the appropriate configuration, can achieve a critical damping ratio that is greater than 0.75, or preferably, greater than or equal to 1.0. ($C/C_C \geq 1$) and, therefore, provide a system where the noise amplification factor is less than one (i.e. noise is attenuated). The first class of material is referred to as a viscoelastic type material. Viscoelastic material exhibits uniquely different behavior under static and dynamic conditions. For example, under a static load, the material exhibits plastic behavior, i.e., it flows slowly and assumes the configuration of the supporting substrate (e.g., the shape of the ear canal entrance). Once conformed to a supporting substrate, the viscoelastic material behaves like any normal plastic material and will not return to its original shape. Under dynamic conditions, however, the viscoelastic material may exhibit brittle behavior. The material sold under the brand name "SILLY-PUTTY™" is an example of a viscoelastic material.

The second class of acceptable material is the normally highly viscous or plastic materials such as soft clay, putty, or bread dough. The highly viscous, plastic and viscoelastic materials will develop values for the damping coefficient (C) that are greater than $C_C$ for all known stethoscope configurations.

The above-mentioned two classes of materials are also important because of their conformal (plastic) properties. They readily adapt to the shape of the supporting substrate (e.g. entrance to ear canal for an in-ear noise barrier apparatus, and area surrounding the ear for an over-the-ear-noise barrier apparatus) and, as a result, form a much better air seal than is possible with the softest elastomer material. Air leakage past the earplug is a serious deficiency associated with elastomer type materials used as earplugs. The perimeter of the elastomer earplug has a tendency to buckle when forced into the ear canal and provide a path for air leakage. Therefore, the system material and configuration should provide an optimal acoustic seal, i.e., prevent any air leakage between the ear canal and the external ambient environment. A small air leak between earplug and flesh can diminish the noise attenuation capabilities substantially. For example, a small 2 mm (0.079 in.) diameter hole in the resulting seal of a typical earplug reduces attenuation performance by approximately 5–15 dB over a wide range of sounds in the lower frequency bands, e.g., below 1000 Hz. Many heart and pulmonary sounds are in the 100 Hz frequency range.

In addition to suppressing (i.e. damping) noise and establishing a good acoustic seal, a third important factor of the present earpiece is comfort. The traditional stethoscope ear tip, e.g. a soft elastomer material/configuration, is very uncomfortable when worn for long periods. Part of this deficiency can be attributed to the elastomer material and part can be attributed to its configuration. For example, the traditional ear tip contacts the user at the entrance to the ear canal. This area is very sensitive and the traditional ear tip presses, i.e., exerts a force, on a relatively small area of the flesh. Thus, the force applied on a small area develops a relatively high pressure (pressure=force/area). The preferred conformal material used in the present invention earpiece, however, slowly conforms to the irregular surface of the outer part of the ear canal and provides a large surface area for the same level of force. As a result, the pressure applied to the outer part of the ear canal is considerably less than the traditional earpiece.

In any case, the cushion 106 preferably comprises material that allows the cushion 106 to easily compress and conform to the shape of the concha and entrance to the ear canal region (18, 28) when the IECR 42 is pressed into the user's ear 10. The cushion 106 thus provides a comfortable interface between the spring-loaded ear tubes 50 and the concha region 28 of the user's ear. When the cushion 106 deforms and conforms to the shape of the user's ear 10, a relatively large area of contact is formed between the cushion 106 and the concha region 18 of the ear 10. The resistance to the spring force by the concha 18 is, therefore, spread over a relatively large area and the actual pressure applied to the concha 18 at any one point is substantially reduced. This lower pressure results in greater comfort for the user.

Thus, cushion 106 is designed to (1) serve as a noise seal, i.e., prevent air and noise leakage between the cushion 106, the concha 18, and the ear canal 30, and (2) serve to dampen any motion caused by the external acoustic pressure wave (noise) that tends to cause the cushion 106 to vibrate, i.e., suppress conduction of external pressure waves to an interior of the cushion. Where the cushion material is sufficiently soft and pliable, it will conform to the shape of the concha 18 and provide an air seal at the entrance 28 to the ear canal 30, thus eliminating or, at least, substantially decreasing the leakage of air. If the cushion material has sufficient noise damping qualities, it will diminish the noise that may be generated by the cushion oscillation. The moldable putty discussed above particularly provides sufficient noise-damping qualities.

FIGS. 7, 8A and 8B illustrate the details of the IEC adapter 96. As mentioned above, the IEC adapter 96 has a tapered plug section 98 and an adapter section 100 with an inner chamber 94. The inner chamber 94 is contoured to substantially match the outer contours of the transducer housing 54 and the end cap 82. In particular, the chamber 94 is circular in cross-section and has a constant diameter (e.g. 0.365 in. (0.927 cm.)) over a substantial portion of its length from the open end 112 toward the inner end 114. Closer to the inner end 114, the chamber 94 has a segment of increased diameter (e.g. 0.436 in. (1.107 cm.)) which defines a circular recess 116 for receiving a flange 118 formed on the end of the transducer housing 54. The remainder 120 of the chamber 94 tapers inward in conformity with the outer shape of the end cap 82.

As shown in FIG. 8A, the outer surface 122 of the adapter section 100 tapers radially outward from the open end 112 to an area 124 where the adapter section 100 intersects with the plug section 98. The adapter section 100 has an outermost diameter of, for example, 0.688 in. (1.75 cm.).

The outer surface 126 of the plug section 98 of the IEC adapter 96 tapers radially inward from the area 124 of intersection with the adapter section 100 to the open end 104. Preferably, the taper has a slight convex curve as shown. The passageway 102 extends through the center of the plug section 98 and is circular in cross-section as shown.

Alternatively, the plug section 98 can be greater in length and smaller in diameter than shown so that it may protrude further into the ear canal 30. FIG. 7 illustrates in phantom an example of a plug section 98' of greater length and smaller diameter. The specific length and thickness of the plug section 98' may depend upon the size of the ear canal 30 and how far the user wishes to insert the plug section 98' into the ear canal 30. In general, a more comfortable and secure fit may be attained the further the plug section is inserted into the ear canal 30 (e.g., in a mid-ear-canal area closer to the ear drum 32).

In the area 124 of intersection between the plug and adapter sections 98, 100, the IEC adapter 96 curves outwardly to form a forward-facing concave indent 128 to match the curvature of the torus-shaped cushion 106. In the embodiment shown in FIGS. 8A, 8B, the indent 128 has a radius of curvature of e.g. 0.065 in. (0.165 cm.). When positioned on the IEC adapter 96, the torus-shaped ear cushion 106 fits partially into the indent 128 as shown in FIG. 5. The radius of curvature of the end of the torus-shaped cushion 106, that is seated in the indent 128, is also e.g. approximately 0.065 in. (0.165 cm.).

The IEC adapter 96 may be made from an elastomer with a softness in the range of 30–40 Shore A Durometer. For an IEC adapter 96 having a longer and thinner plug section 98', the IEC adapter, however, may be made from a softer elastomer so that the plug section 98' can bend more easily as it is inserted into the user's ear canal 30.

As discussed further above, when the user inserts the plug section 98 (98') into the ear 10, the ear cushion 106 contacts the concha region 18 of the outer ear. The pressure from the ear-tube spring mechanism 52 causes the cushion 106 to substantially deform and assume the shape of the concha region 18. The area of contact between the cushion 106 and the concha region 18 is relatively large, resulting in the spring force being distributed over a relatively large area. This large distributed area of force further results in a much lower unit of pressure being applied to the flesh around the entrance to the ear canal. Preferably, the cushion 106 is made large enough to reduce or eliminate the amount of contact between the plug section 98 and the entrance 28 to the ear canal 30. In other words, the cushion 106 preferably is sized to receive and distribute to the concha region 18 of the ear 10 a substantial amount of the force being applied by the ear-tube spring mechanism 52.

The earpiece assembly 108 (i.e., IEC adapter 96 and ear cushion 106) may also be adapted for use as a comfortable ear plug for blocking the entrance of noise into the user's ear canal 30. Preferably, the earpiece would have the longer and thinner plug section 98' shown in FIG. 7. The chamber 94 of the IEC adapter 96 may be filled with a sound absorbing material, or the adapter 96 can be formed into a solid piece.

With reference to FIG. 4, the details of the transducer housing 54 will be explained. In the embodiment shown, the transducer housing 54 is made from aluminum but may be made from other suitable materials such as engineering grade plastic. As mentioned above, the transducer housing 54 has first and second cylindrical inner chambers 64, 66, respectively. The housing 54 is symmetrical about its longitudinal axis with its outer surface being circular in cross-section along its length. The outer surface further has a first segment 130 that is relatively short in length (e.g. 0.037 in. (0.094 cm.)) and defines the flange 118. The diameter of the flange 118 is e.g. 0.436 in. (1.107 cm.). When the housing 54 is inserted into the IEC adapter chamber 94, the flange 118 is received into the chamber recess 116 so that the segment 130 is essentially press-locked in place.

The outer surface of the housing 54 further has a second segment 132 of smaller diameter (e.g. 0.365 in.; 0.927 cm.) but greater length (0.704 in.; 1.788 cm.) than the first segment 130. The second segment 132 has a knurled surface which enables the walls of the IEC adapter chamber 94 to better grip the transducer housing 54. The knurled surface also provides a rough surface that enhances cement bonding if the IEC adapter 96 is bonded to the housing 54. As mentioned further above, however, the IEC adapter 96 may be merely press fit onto the transducer housing 54 so that the IEC adapter 96 may later be removed if desired; in which case, the knurled surface helps prevent sliding of the adapter 96 about the housing 54.

The outer surface of the housing 54 has a third segment 134 of greater diameter (e.g. 0.436 in.; 1.107 cm.), equal to the diameter of the first or flange segment 130, and a relatively short length (e.g. 0.094 in.; 0.239 cm.). The edge 136 of the third segment 134 forms a lip which engages the outer end 140 of the IEC adapter 96. Lastly, the outer surface of the housing 54 has a fourth segment 142 which tapers inward from the third segment 134. In the embodiment shown, the fourth segment 142 tapers at an angle of thirty degrees (30°).

FIGS. 9A, 9B, 10, and 11A–D illustrate the details of the components of the encapsulated transducer assembly 76. FIGS. 9A and 9B illustrate the details of the end cap 82. The end cap 82 includes: a cylindrical portion 144 which fits into the circular passageway 102 of the IEC adapter 96; a tapered disk portion 146 which fits into the tapered portion 120 of the IEC adapter chamber 94; and a short rectangular portion 148 which fits into the hole 80 (which is rectangular) of the transducer adapter body 78 and receives the audio output 110 of the transducer 56. The through hole 84 passes through the center of the end cap 82. The central axis R of the rectangular portion 148, however, is slightly offset from the central axis X of the end cap 82. In particular, the central axis R of the rectangular portion 148 is offset downward e.g. 0.014 in. (0.0356 cm.) from the central axis X as shown in FIG. 9B (axis X is shown going into the page in FIG. 9B). Preferably, the end cap 82 is made from plastic but may be made from other suitable materials as well.

FIGS. 11A–11D illustrate the details of the transducer adapter body 78. The transducer adapter body 78 is cylindrical in shape with the rectangular hole 80 passing through its length. The adapter body 78 is made thicker on one side 150 so that the central axis H of the rectangular hole 80 is positioned slightly off center of the central axis Y of the transducer adapter body 78 as shown in FIG. 11C. The offset of the rectangular hole 80 is equal to the offset of the rectangular portion 148 of the end cap 82. As explained further below, the offsets help to properly align the transducer 56 so that the audio output 110 is aligned with the central axis X of the end cap 82. When the end cap 82 is positioned on the end of the transducer adapter body 78, the central axes X and Y are aligned, and the rectangular portion 148 and the rectangular hole 80 are aligned. Preferably, the transducer adapter body 78 is made from plastic or other material similar to the material of the end cap 82.

FIGS. 10 and 11A–11D illustrate the general positioning of the transducer 56 within the transducer adapter body 78. In the present embodiment, the transducer 56 is an electrodynamic type speaker. An example of such a transducer 56 is model number ECA-3132 electrodynamic speaker available from Knowles Electronics, Inc. of Itasca, Ill. The transducer 56 is generally rectangular in shape and includes two contact points or mounts 88 to which the ends of the conductors 82 may be soldered. On the opposing end is the signal output port 110 which focuses the broadcast sound signal in the direction indicated by arrow S shown in FIGS. 11A and 11D.

The signal output port 110 is slightly offset upwardly from the central axis Z of the transducer 56 as shown in FIG. 11B (axis Z is shown into the page in FIG. 11B). Due to the downward offset of the through hole 80 of the transducer adapter body 78, however, the signal output port 110 is aligned with the central axis Y of the transducer adapter body 78 when the transducer 56 is inserted into the through hole 80. When the IECR 42 is fully assembled, the signal output port 110 is received in the through hole 84 of the end cap 82 and is aligned with the central axis X of the end cap 82.

The through hole 80 of the transducer adapter body 78 may be filled with epoxy in order to fix the positioning of the transducer 56 within the through hole 80. By filling the through hole 80 with the epoxy, short sections 156 of the leads 86, adjacent the contacts 88 and solder joints, will also be covered and afforded protection against external stresses that may be applied to the wire 86.

As described above, the two conductor wires or leads 86 are hard wired (e.g., soldered) to the transducer 56. These leads 86 are very thin and are preferably twisted to form a rope-like construction. In order to protect the leads against undue torsional stresses, the leads 86 are preferably twisted in a direction so that the leads will have a tendency to unwind rather than twist further when the stethoscope tube 50 and transducer housing 54 are threaded together. For example, the leads 86 would be carefully twisted in a counterclockwise direction where the end of the ear tube 50 is threaded in a clockwise direction. To further protect the wires 86 from torsional or other stresses, the wires 86 may be encased in a shielded cable that is fed through the ear-tube 50. In addition, as described above, the transducer 56 and a section 156 of the leads 86 adjacent the contacts 88 are encapsulated in the transducer adapter body 78 and surrounded by epoxy. The encapsulation of the section 156 of the wires 86 provides additional protection against stress being applied to the wires 86 at the solder joints.

FIGS. 12A–C illustrate another embodiment of an encapsulated transducer assembly 160 that may be used in place of the encapsulated transducer assembly 76 shown in FIG. 10. FIGS. 12A–C in particular illustrate the assembly process for inserting the encapsulated transducer assembly 160 into a modified transducer housing 54'. The transducer housing 54' is similar to the transducer housing 54 shown in FIG. 4 with the exception that the second chamber 66' and the passageway 90' have been modified as explained further below. In this embodiment, the transducer 56, rather than being encapsulated in the adapter body 78 and end cap 82, is encapsulated in a molded, solidified encapsulant or housing 162. An example of a suitable material for encapsulating the transducer is an epoxy potting compound. Many well known thermoplastic and thermosetting materials exist, however, that would be suitable for forming the solidified encapsulant 162.

In production, the pre-wired transducer 56 (i.e., the transducer 56 with the twisted wires 86 or shielded cable attached thereto) is inserted into a mold and a plastic potting compound is poured or injected into the mold. The soldered wire terminals 164 and a short length 166 of the twisted wires 86 are also encapsulated in the potting compound in order to form a strain relief. By encapsulating the soldered joints 164 and a section 168 of the wires 86, any torsional displacement applied to the wires 86 external to the encapsulant 162 will not be transmitted to the wires 86 at the terminals 164 and, therefore, cannot cause any stress at the soldered joint 164. This stress relief is important as the wires 86 typically would be made from copper which can become embrittled after being subjected to heat. The copper wire immediately adjacent the terminal 164 would be particularly subjected to the heat of the molten solder and may become embrittled in an area known as the "heat affected zone". This embrittled, heat affected zone, would be more likely to break if subjected to undue stresses. By encapsulating a length 166 of the wires 86 that includes this zone, ample protection against breakage can be obtained.

The encapsulant or encapsulated housing 162 is molded so that its outer shape is generally symmetrical about its central longitudinal axis M. The shape is generally cylindrical with an outermost diameter slightly smaller than the inside diameter of the second chamber 66' of the transducer housing 54'. In addition the outer shape of the cylindrical encapsulant 162 at the solder terminal end 164 preferably tapers down to a diameter slightly larger than the diameter of the twisted wire bundle, i.e., has a cone shape. The tip of the cone-shaped protuberant 168 is aligned with central longitudinal axis M resulting in the wires 86 extending slightly upward from the soldered joint 164 as shown in FIGS. 12A–C. The cone-shaped protuberant 168 may then mate with a corresponding concave cone shape 170 formed at the inner end of the second chamber 66' of the transducer housing 54'.

At the opposing end 172, a thin cylindrical tube 174 is placed about the audio output 110 of the transducer 56 and is also encapsulated in the potting compound. The tube 174 provides an audio passage 176 for sounds emitted from the transducer 56 and improves the structural integrity of the housing 162 near the audio end 172 so that the assembly may be safely fit into the IEC adapter 96. In addition, the outer shape of the end 172 is similar to the outer shape of the end cap 82 of the encapsulated assembly of FIG. 10 to further facilitate insertion of the assembly into the adapter 96. As shown in FIGS. 12A–C, the tube 174 is aligned with the central longitudinal axis M of the encapsulated housing 162. In order to obtain the alignment, the encapsulated housing 162 is made thinner on the bottom as viewed in FIGS. 12A–C.

The outer surface of the cylindrical encapsulant 162 and/or the inner surface of the second chamber 66' of the transducer housing 54' may be lubricated to facilitate the assembly process. Thus, when the transducer housing 54' is threaded onto the ear tube terminal 58, the cylindrical encapsulant 162 is free to rotate, and the strain on the wires 86 is minimized. If the friction is too great and the encapsulant cylinder 162 resists rotation, the previously twisted wires 86 may tend to unwind (if wound in a direction opposite the direction of twisting of the transducer housing 54') or may be subjected to additional twisting forces (if wound in the same direction of twisting as the transducer housing 54'). The combination of the encapsulation of the transducer 56' as described above and the lubrication of the resulting encapsulant 162 results in a robust product that can sustain the rigors of rough handling. As the outer configuration of the transducer housing 54' is similar to the outer configuration of the transducer housing 54 shown in FIG. 4, the assembled transducer assembly 92' may be easily substituted for the transducer assembly 92 of the IECR 42.

Figure 13:
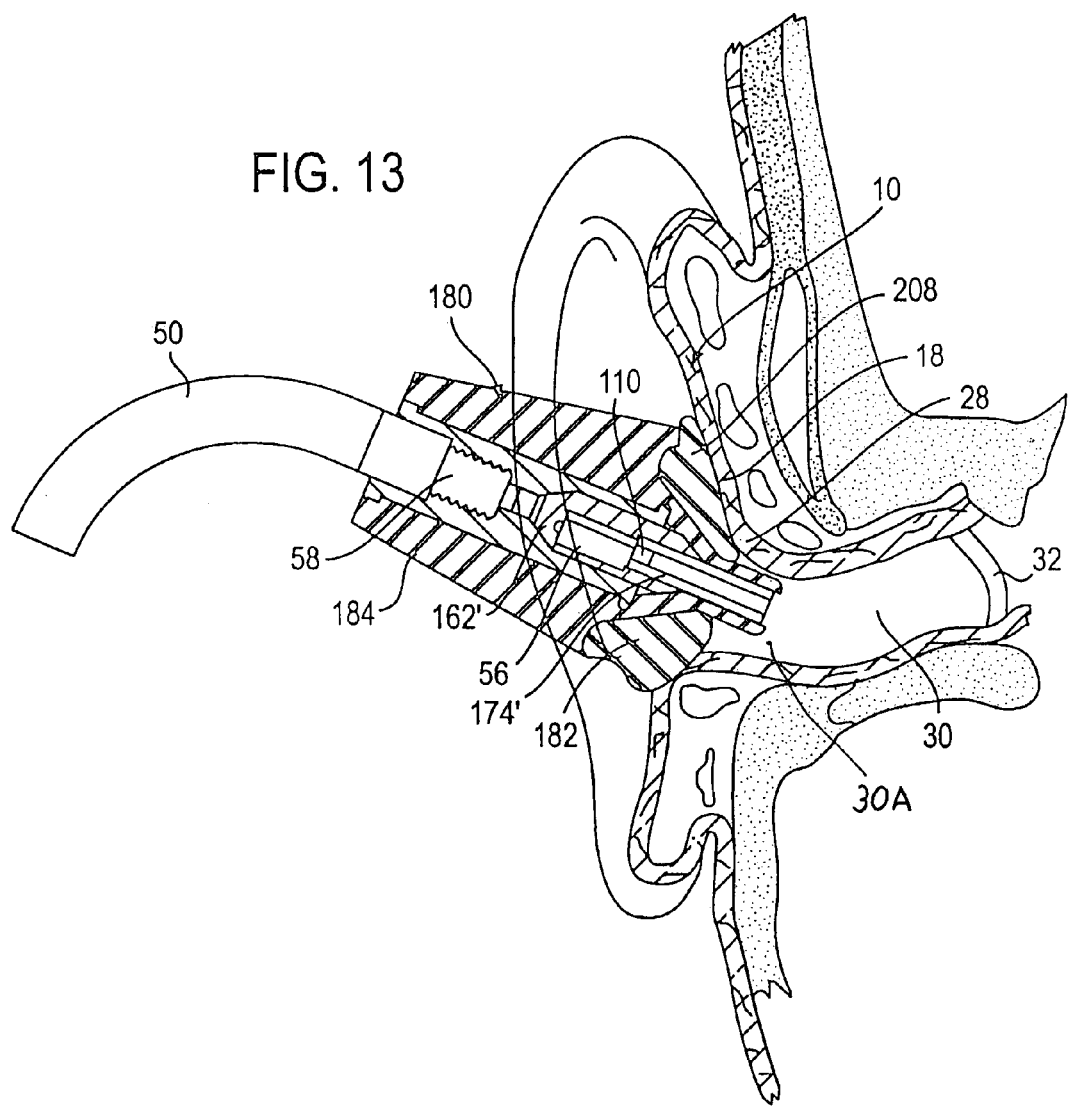
FIG. 13 is a side cross-sectional view of another embodiment of an IECR positioned in a human ear.
Figure 14:
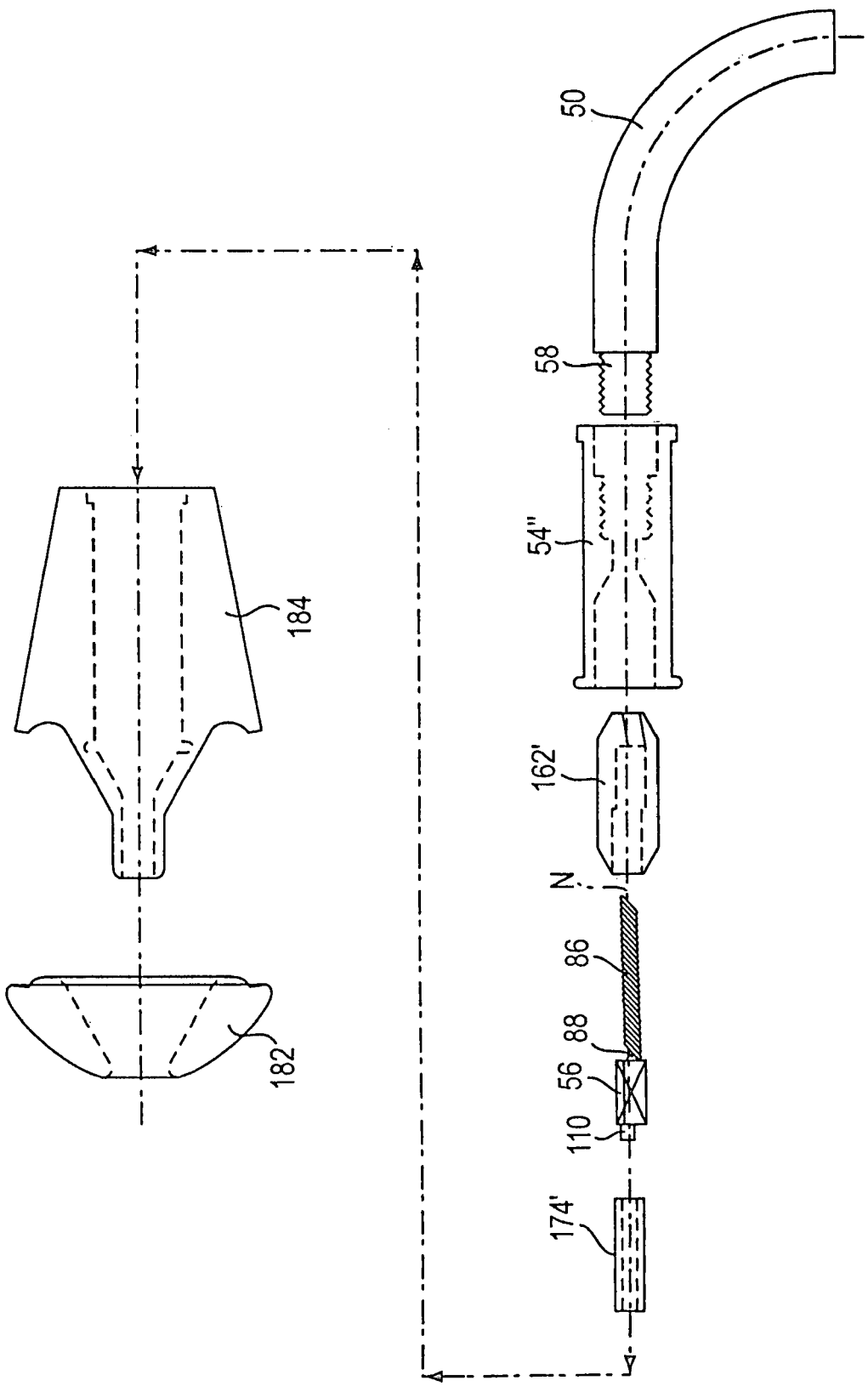
FIG. 14 is an exploded side view of the IECR of FIG. 13.
Figure 15:
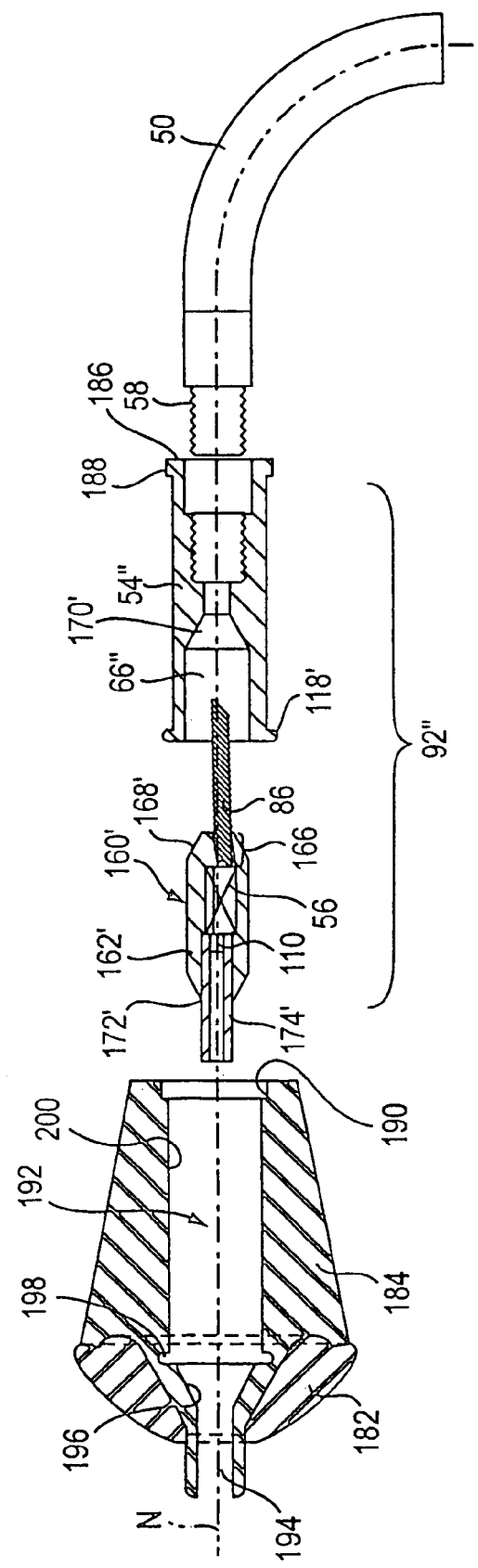
FIG. 15 is an exploded side cross-sectional view of the IECR of FIG. 13.

FIGS. 13–15 illustrates another embodiment of an IECR 180 that has a contoured ear cushion 182 and IEC adapter 184. The IECR 180 comprises a modified encapsulated transducer assembly 160' (FIG. 15) that is similar to the encapsulated transducer assembly 160 shown in FIGS. 12A–C except where noted below. The encapsulated transducer assembly 160' includes a transducer 56 pre-wired with conductor leads 86. Positioned about the audio output 110 of the transducer 56 is a relatively long, thin cylindrical audio tube 174'. The transducer 56, audio tube 174' and a short length 166 of the conductor wires 86 are encapsulated in a solidified encapsulant or encapsulating housing 162' formed from a plastic potting compound in a manner described above with reference to FIGS. 12A–C.

The outer shape of the encapsulant 162' of FIGS. 13–15 is generally cylindrical and symmetrical about a central longitudinal axis N. The wired end of the encapsulant 162' tapers into a conical protuberant 168' much like the conical protuberant 168 of the encapsulant 162 of FIGS. 12A–C. The audio end 172' has been modified, however, so that the audio tube 174' extends beyond the encapsulated housing 162' and the encapsulated housing 162' tapers inward to the outer surface of the audio tube 174'.

The conical protuberant end 168' of the encapsulant 162' is fit into the second chamber 66'' of a transducer housing 54''. The transducer housing 54'' is similar to the transducer housing 54' of FIGS. 12A–C having a second chamber 66' with a concave conical inner end 170'. The exterior of the end 186 of the transducer housing 54'', however, has been slightly modified to provided an annular flange 188 which mates with a counter bore 190 provided in IEC adapter 184. As shown in FIGS. 13–15, the transducer housing 54'' may be threaded onto the end of the stethoscope tube 50.

The fully assembled transducer assembly 92'' (encapsulated assembly 160' and transducer housing 54'') may be press fit into the inner chamber 192 of the IEC adapter 184. The inner chamber 192 has a contour that corresponds to the outer contour of the transducer assembly 92''. In particular, the inner chamber 192 has a cylindrical audio passage 194 for receiving the exposed section of the audio tube 174', a concave conical section 196 for receiving the audio conical end 172' of the encapsulant 162', an annular indent 198 for receiving the flange 118' of the transducer housing 54'', a straight cylindrical section 200, and the counter bore 190. As explained in more detail below, the exterior of the IEC adapter 184 has been modified to accommodate the contoured ear cushion 182.

Figure 16B:
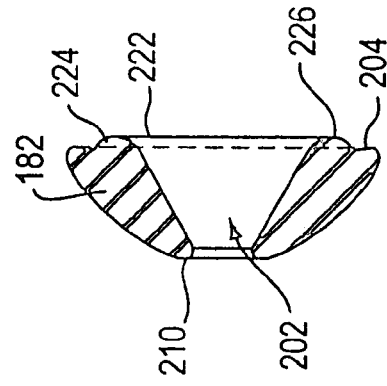
FIG. 16B is side cross-sectional view of the contoured ear cushion taken along section A—A of FIG. 16A.
Figure 16D:
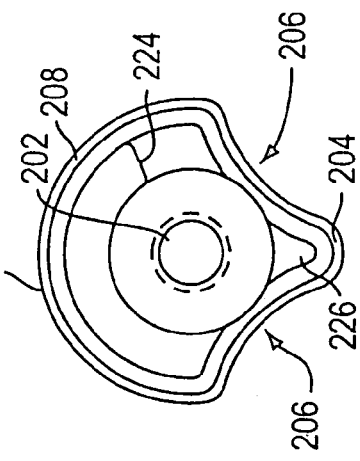
FIG. 16D is a rear end view of the contoured ear cushion of FIG. 16A.
Figure 16A:
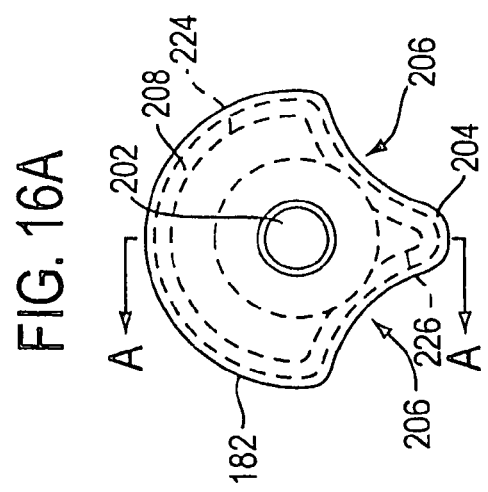
FIG. 16A is a front end view of a contoured ear cushion forming a portion of the IECR of FIG. 13.
Figure 16C:
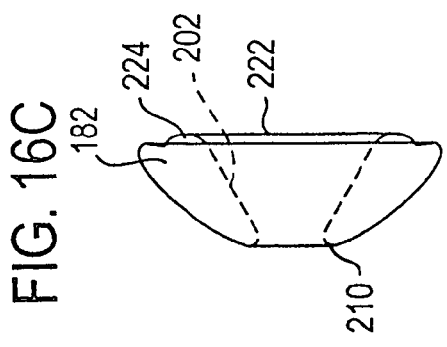
FIG. 16C is a side view of the contoured ear cushion of FIG. 16A.

With reference to FIGS. 16A–D, the ear cushion 182 has a generally "sea-shell" shape with a central through hole 202 and comprises a soft pliable material as described with reference to the cushion 106 of FIG. 3. As shown in FIGS. 16A and 16D, the cushion 182 has generally a sea-shell shape with a protruding notch 204 defined by two indented sections 206. The opposing side 208 of the cushion 182 has generally a semi-circular configuration as shown in FIGS. 16A and 16D. In addition, as shown in FIGS. 16B and 16C, the outer surface of the cushion 182 and the central through hole 202 taper inwardly toward the front end 210 of the cushion. As explained further below, when the IECR 180 is inserted into the user's ear 10, the semi-circular side 208 is pressed against the concha region 18, and the notch 204 is fit into the iscisua or notch 26 between the tragus 22 and antitragus 24 of the ear 10.

Figure 17C:
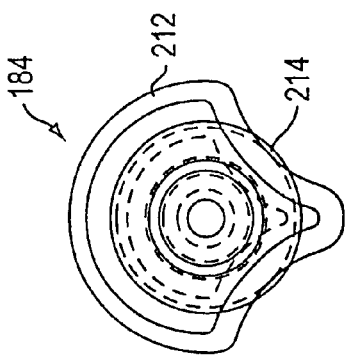
FIG. 17C is rear end view of the IEC adapter of FIG. 17A.
Figure 17B:
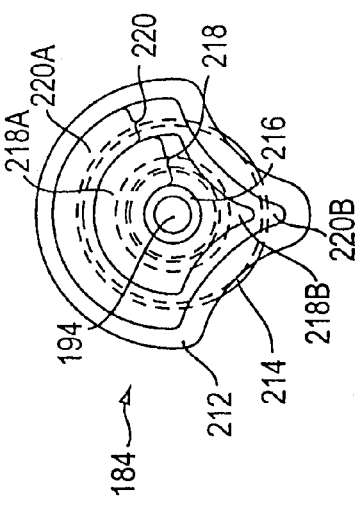
FIG. 17B is front end view of the IEC adapter of FIG. 17A.
Figure 17A:
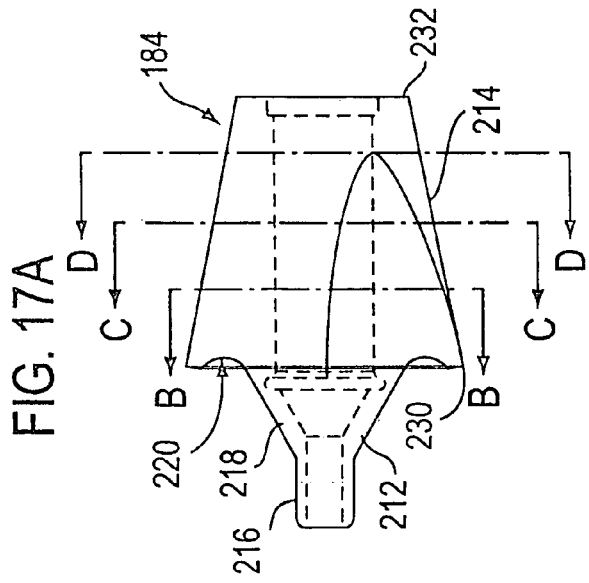
FIG. 17A is a side view of an IEC adapter forming a portion of the IECR of FIG. 13.
Figure 17F:
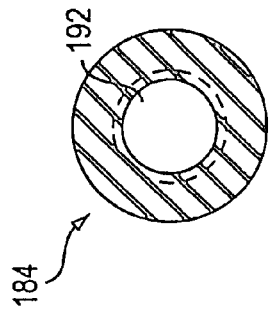
FIG. 17F is cross-sectional view taken along line D—D of FIG. 17A.
Figure 17E:
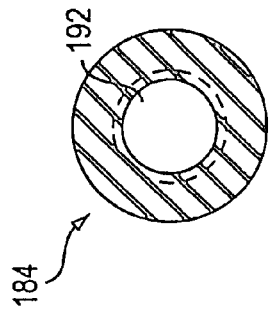
FIG. 17E is cross-sectional view taken along line C—C of FIG. 17A.
Figure 17D:
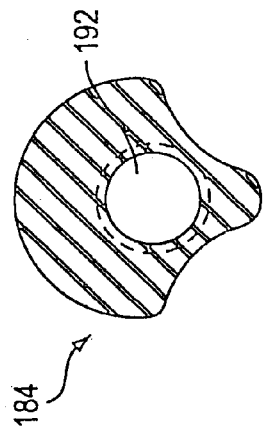
FIG. 17D is cross-sectional view taken along line B—B of FIG. 17A.

As mentioned above, the IEC adapter 184 has been configured to accommodate the contoured cushion 182. With reference to FIGS. 17A–17F, the IEC adapter 184 has a cushion-supporting section 212 and an adapter section 214. The cushion-supporting section 212 has a cylindrical audio segment 216 of reduced diameter, a tapered cushion-receiving segment 218, and a forward-facing, concave segment 220. As shown in FIG. 17B, the cushion-receiving segment 218 and concave segment 220 both have generally a "sea-shell" configuration with a semi-circular side (218A, 220A) and a "notched" side (218B, 220B).

With reference to FIGS. 16A–D, the rear end 222 of the ear cushion 182 has a protruding section 224 on its semi-circular side 208 that is received in the semi-circular side 220A of the IEC adapter concave segment 220. The ear cushion 182 further has a protruding notch 226 that is received in the "notched" side 220B of the IEC adapter concave segment 220. The tapered through hole 202 of the cushion 182 is shown having a generally cylindrical configuration which, due to the cushion material, may be easily pressed about the cushion-receiving segment 218 of the IEC adapter 184 to conform with the shape of the cushion-receiving segment 218.

As shown in FIGS. 17A and 17D–F, the outer surface of the adapter section 214 of the IEC adapter 184 is contoured so that its cross-section progresses from a sea-shell configuration at the adapter section's forward end 230 to a circular configuration at its rear end 232. This configuration prevents the adapter section 214 from interfering with the user's ear 10 when the IECR 180 is inserted in the user's ear and provides a more finished appearance to the assembly 180.

With reference to FIG. 13, when the IECR 180 is inserted into the user's ear 10, the cushion 182 is pressed against the concha region 18 at the entrance 28 to the ear canal 30. The cushion 182 deforms to the shape of the surface of the ear and establishes a good seal about the entrance 28 to the ear canal 30. The large, semi-circular side 208 of the cushion 182 in particular fills the concha region 18, reducing the pressure applied to the concha 18 and entrance 28 to the ear canal 30 by the stethoscope spring mechanism 52. The cushion 182 also prevents or substantially reduces contact between the IEC adapter 184 and the concha 18 and entrance 18 to the ear canal, thus providing a more comfortable fit.

Figure 18:
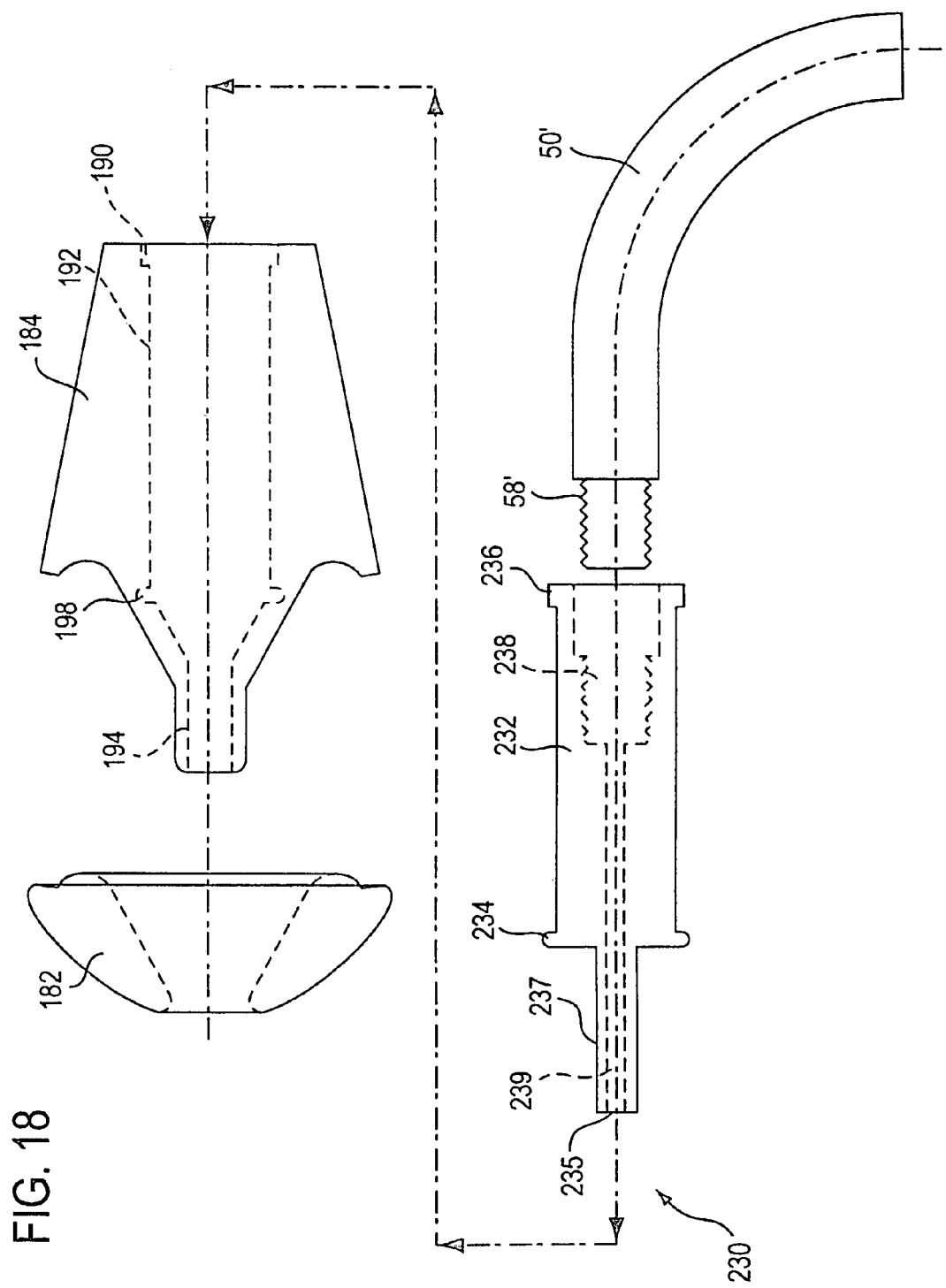
FIG. 18 is an exploded side view of another embodiment of an IECR that may be used with a traditional, mechanical stethoscope.
Figure 20:
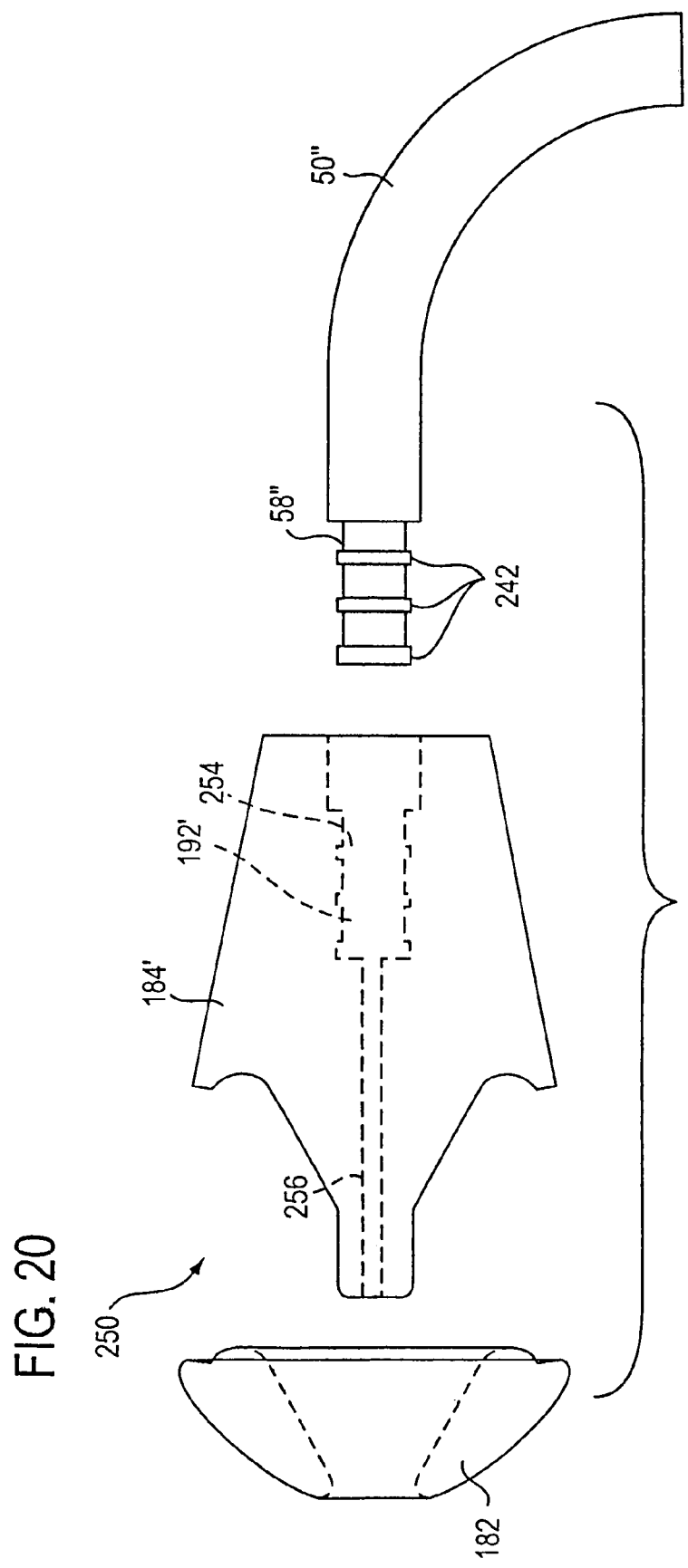
FIG. 20 is an exploded side view of another embodiment of an IECR that may be used with a traditional, mechanical stethoscope.

FIGS. 18–20 illustrate additional embodiments of IECRs 230, 240, and 250, respectively, that may be used with a more conventional, mechanical stethoscope that transmits audio signals from the stethoscope head to the earpiece via a column of air in the ear tube 50'. The outer configuration of each of the IECRs 230, 240, and 250 is similar to the outer configuration of the IECR 180 shown in FIG. 13. The interior configurations, however, have been modified as these IECRs 230, 240, and 250 do not house transducers.

With reference to FIG. 18, IECR 230 comprises an ear cushion 182, identical to the ear cushion 182 shown in FIGS. 13–15, and an IEC adapter 184 that is identical to the IEC adapter 184 shown in FIGS. 13–15. The IECR 230 further has a cylindrical mounting adapter 232 with flanges 234, 236 that respectively fit in the indent 198 and counterbore 190 of the IEC chamber 192. The mounting adapter 232 further has an audio segment 237 of greatly reduced diameter, which is received in the audio passage 194 of the IEC adapter 184.

The mounting adapter 232 also has a mounting chamber 238, similar in configuration to the second chamber 64 of the IECR 42 shown in FIG. 4, that allows the mounting adapter 232 to be threaded onto the end 58' of a mechanical stethoscope 50'. A thin audio passage 239 couples the mounting chamber 238 to an opening 235 at the forward end of the housing 232 and allows passage of the audio signal transmitted by the ear tube 50' through the adapter 232 and out the opening 235.

The IECR 240 of FIG. 19 is identical to the IECR 230 of FIG. 18 except that the mounting chamber 238' of the mounting adapter 232' has been modified to accommodate a different terminal configuration for the end 58" of the stethoscope tube 50". The end 58" of the stethoscope tube 50" is provided with several annular ridges 242 that are press fit into corresponding annular indents 244 provided in the mounting chamber 238'.

The IECR 250 of FIG. 20 is similar to the IECR 240 of FIG. 19 except that the IECR 250 does not have a mounting adapter 232'. Rather, the interior chamber 192' of the IEC adapter 184' is shaped in a manner similar to the shape of the interior of the adapter housing 232' of the IECR 240 so that the IEC adapter 184' may directly receive the end 58" of the stethoscope tube. In particular, the chamber 192' of the IEC adapter 184' has a mounting chamber 254 that is identical to the mounting chamber 238' of FIG. 19 and an audio tube 256 identical to the audio tube 239 of FIG. 19.

It should be noted that the mounting chamber 254 of the IEC adapter 184' of FIG. 20 may alternatively be provided with mounting threads so that the adapter 184' may be threaded onto the end of a threaded stethoscope tube. Furthermore, the IECR 250 may be modified for use with an electronic stethoscope. In particular, the interior chamber 192' of the IEC adapter 184' may be modified to include a transducer chamber shaped to receive and hold an encapsulated transducer assembly (76, 160, or 160'). Such a modified IECR would not have a separate transducer housing (54, 54', or 54")

Figure 25:
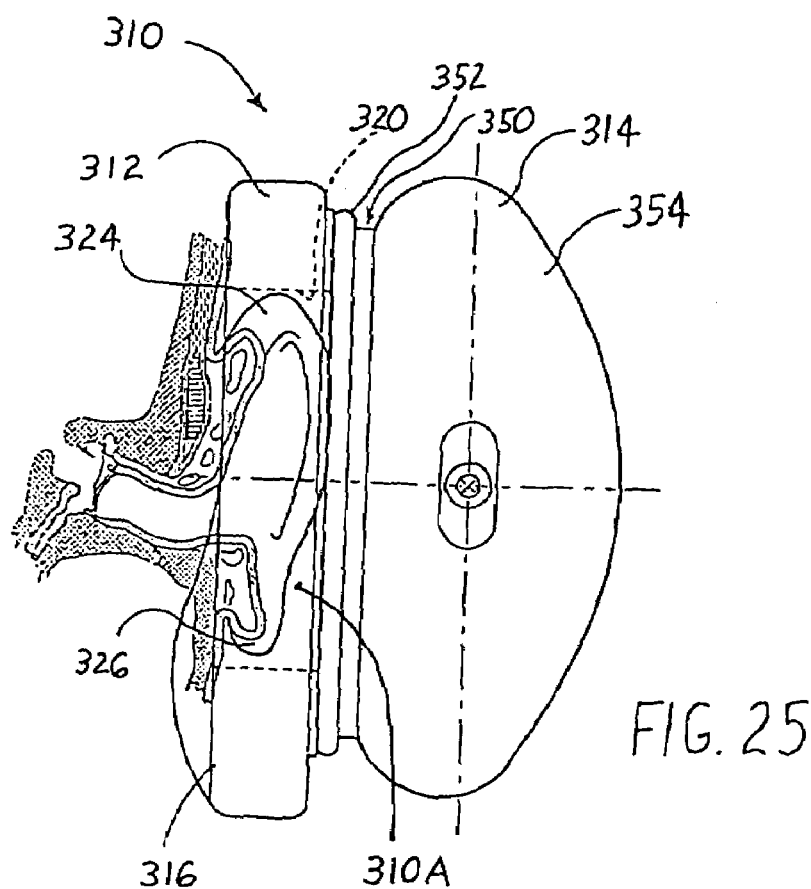
FIG. 25 is a partially cross-sectional front view of an essential portion of an over-the-ear noise barrier apparatus applied on a user's ear.

According to another aspect of the present invention, FIGS. 25–29 show an over-the-ear noise barrier apparatus 365, which can configured as a headset or ear defender. The headset 365 illustrated in FIG. 26 is shown to include a pair of ear cup assemblies 310 connected together by an ear cup bridge (or headband) 362 via pivots 364. As best illustrated in FIG. 25, each ear cup assembly 310 includes an ear cup 314 to be held over the user's outer ear 324 via a circumaural audio seal (or cushion) 312. The ear cup 314 includes a dome-like outer cover section 354, an ear cup flange 352 to which the circumaural cushion 312 is secured, and a flat, rigid or semi-rigid, torus-like interface section 350 connecting the ear cup flange 352 to the outer cover section 354.

The circumaural cushion 312 of this over-the-ear apparatus corresponds to the concha cushion (e.g. 106) of the in-ear apparatus discussed above. The materials and acoustic characteristics of the circumaural cushion 312 are thus the same or similar to those of the concha cushion of the in-ear apparatus. Of course, however, the design of the circumaural cushion 312 must be adapted to fit over and in surrounding relation to the user's outer ear, so as to be comfortable and provide an excellent audio seal to prevent leakage of air and sound to an interior of the cushion 312 (i.e. to an audio chamber 310A defined by the ear cup 314 and including the ear canal). In view of these considerations, the circumaural cushion 312 is preferably torus-shaped so as to properly surround the user's outer ear 324 including the ear lobe 326. Although generally torus-shaped according to the preferred form of the cushion 312, the cushion preferably includes a bulging neck/head pad section 316 which protrudes generally downwardly and rearwardly, and also bulges inwardly towards the user's head, as best shown in FIGS. 25 and 27–29.

While several embodiments of the invention, including various modifications, have been shown and described, it should be recognized that other variations, substitutions, or modifications will occur to those skilled in the art. For example, the specific dimensions of the invention may vary from the examples described herein. Furthermore, different features of certain of the embodiments may be substituted for similar type features in other embodiments, e.g., the mounting arrangement illustrated in FIG. 19 may be used for the other in-ear embodiments as well. Any such variations, substitutions, and modification are intended to fall within the scope of the invention.

What is claimed is:

1. A noise barrier apparatus for preventing external noise from causing noise in an ear on a side of a user's head, the noise barrier apparatus comprising:
   an ear adapter body having a first end and a second end forward of said first end and insertable into the ear canal of the ear, said ear adapter body defining an enclosed audio chamber including the ear canal of the ear, said ear adapter body further having,
   an ear canal section adjacent said second end,
   an outer ear section adjacent said first end, and
   a concha section disposed between said ear canal and outer ear sections, whereby said ear canal section is disposed in the ear canal of the ear, the concha section is disposed adjacent the concha region of the ear, and the outer ear section is disposed outside the ear when said second end of said ear adapter body is inserted into the ear canal of the ear; and
   a separate concha cushion to bear against the concha region of the ear, said concha cushion being mounted onto said concha section of said ear adapter body and positioned thereon so as to be interposed between the concha region of the ear and said concha section and being configured to encircle the ear canal entrance when said second end of said ear adapter body is inserted into the ear canal,
   said concha cushion being deformable so as to be conformable to the concha region of the ear when held thereagainst.

2. The noise barrier apparatus of claim 1 wherein said concha cushion comprises a material which is at least partially plastically deformable.

3. The noise barrier apparatus of claim 2 wherein said material of said concha cushion further comprises an at least partially plastically deformable material contained in a flexible sheath.

4. The noise barrier apparatus of claim 2 wherein said material of said concha cushion provides a damping ratio greater than or equal to 0.75.

5. A noise barrier apparatus for preventing external noise from causing noise in ears on opposing sides of a user's head, each of the ears having a concha region opening into an ear canal, said noise barrier apparatus comprising:
   a pair of noise barrier devices to be held against the opposing sides of the user's head and engaged with the concha regions of the respective ears;
   a noise barrier device holding apparatus coupled to said noise barrier devices to hold said noise barrier devices against the opposing sides of the user's head and against the concha regions of the respective ears;
   wherein said noise barrier devices each respectively comprise,
      an ear adapter body having a first end and a second end forward of said first end and insertable into the ear canal of a respective one of the ears, said ear adapter body further having,
      an ear canal section adjacent said second end,
      an outer ear section adjacent said first end, and
      a concha section disposed between said ear canal section and said outer ear section,
         whereby said ear canal section is disposed in the ear canal of a respective ear, the concha section is disposed adjacent the concha region of the respective ear, and the outer ear
         section is disposed outside the respective ear when said second end of said ear adapter body is inserted into the respective ear canal of the respective ear, and
      a separate concha cushion mounted onto said concha section of said ear adapter body, said concha cushion being positioned on said ear adapter body so as to be interposed between the concha region of the ear and said concha section and to encircle the ear canal of the ear when said second end of said ear adapter body is inserted into the ear canal,
         said concha cushion being deformable so as to conform to the concha region of the ear.

6. The noise barrier apparatus of claim 5 wherein said concha cushion is of a material which is at least partially plastically deformable.

7. The noise barrier apparatus of claim 6, wherein each of said concha cushions is fabricated from a material which is at least partially plastically deformable and is encased in a flexible sheath.

8. The noise barrier apparatus of claim 6 further wherein each said concha cushion has a damping ratio greater than 0.75.

9. The noise barrier apparatus of claim 8, wherein each said concha cushion is fabricated from a material which is at least partially plastically deformable and encased in a flexible sheath.

10. The noise barrier apparatus of claim 9, wherein said noise barrier device holding apparatus further comprises:
    ear tubes of a stethoscope.

11. The noise barrier apparatus of claim 8 further wherein each said concha cushion has a damping ratio greater than 1.0.

12. The noise barrier apparatus of claim 11, wherein each said concha cushion is fabricated from a material which is at least partially plastically deformable and encased in a flexible sheath.

13. The noise barrier apparatus of claim 6, wherein said noise barrier device holding apparatus further comprises:
    ear tubes of a stethoscope.

14. The noise barrier apparatus of claim 5, wherein said noise barrier device holding apparatus further comprises:
    ear tubes of a stethoscope.

* * * * *